(12) United States Patent
Shakfeh

(10) Patent No.: US 11,615,473 B2
(45) Date of Patent: Mar. 28, 2023

(54) RESILIENCE MEASUREMENT SYSTEM

(71) Applicant: Noor Shakfeh, Spring Hill, FL (US)

(72) Inventor: Noor Shakfeh, Spring Hill, FL (US)

(73) Assignee: Noor Shakfeh, Spring Hill, FL (US)

( * ) Notice: Subject to any disclaimer, the term of this patent is extended or adjusted under 35 U.S.C. 154(b) by 0 days.

(21) Appl. No.: 17/192,801

(22) Filed: Mar. 4, 2021

(65) Prior Publication Data
US 2021/0279804 A1    Sep. 9, 2021

Related U.S. Application Data

(60) Provisional application No. 62/985,842, filed on Mar. 5, 2020, provisional application No. 63/066,284, filed on Aug. 16, 2020.

(51) Int. Cl.
   *G06Q 10/10*    (2012.01)
   *G06Q 10/06*    (2012.01)
   (Continued)

(52) U.S. Cl.
   CPC .......... *G06Q 40/06* (2013.01); *G06F 16/951* (2019.01); *G06N 20/00* (2019.01); *G06Q 10/067* (2013.01);
   (Continued)

(58) Field of Classification Search
   CPC ............... G06Q 40/06; G06Q 50/26; G06Q 10/06375; G06Q 40/08; G06Q 10/067;
   (Continued)

(56) References Cited

U.S. PATENT DOCUMENTS 6,856,973 B1   2/2005 Bott
7,181,428 B2   2/2007 Lawrence
(Continued)

FOREIGN PATENT DOCUMENTS

CN   109840271 A   6/2019
EP    1577818 A1   9/2005
(Continued)

OTHER PUBLICATIONS

A. Shell, AA Free, "Why aren't advisers warming up to ESG? For ESG funds to attract more dollars, advisers are going to have to have to embrace the concept more enthusiastically than they have in the past," Oct. 5, 2019, 3 pages, https://www.investmentnews.com/why-arent-advisers-warming-up-to-esg-169845.

(Continued)

*Primary Examiner* — Jonathan P Ouellette
(74) *Attorney, Agent, or Firm* — Squire Patton Boggs (US) LLP

(57) ABSTRACT

Certain example embodiments provide systems, methods, apparatuses, and computer program products for a resilience measurement system. For example, the resilience measurement system may receive data from multiple sources, and may measure resiliency based on this data, such as the ability of a population or geographic area (e.g., a country) to withstand emerging threats, including but not limited to, posed by climate and environment, health, globalization, and human development. The resilience measurement system may calculate one or more scores indicating risk, need for program adjustment, or need for policy change and investment, depending on the client the project. To perform such operations, the resilience measurement system may process index scores for different categories of threats to average the index scores for different categories of threats with different weights. The final scores may be used by the resilience measurement system for additional analysis, to perform actions, and/or the like.

22 Claims, 8 Drawing Sheets

(51) Int. Cl.
  *G06Q 30/06* (2012.01)
  *G06Q 30/02* (2012.01)
  *G06Q 40/06* (2012.01)
  *G16H 50/30* (2018.01)
  *G16H 50/80* (2018.01)
  *G16H 50/70* (2018.01)
  *G16H 50/20* (2018.01)
  *G06F 16/951* (2019.01)
  *G06Q 40/08* (2012.01)
  *G06Q 10/067* (2023.01)
  *G06Q 10/0637* (2023.01)
  *G06N 20/00* (2019.01)
  *G06Q 50/26* (2012.01)

(52) U.S. Cl.
  CPC ....... *G06Q 10/06375* (2013.01); *G06Q 40/08* (2013.01); *G06Q 50/26* (2013.01); *G16H 50/20* (2018.01); *G16H 50/30* (2018.01); *G16H 50/70* (2018.01); *G16H 50/80* (2018.01)

(58) Field of Classification Search
  CPC ........ G16H 50/20; G16H 50/80; G16H 50/30; G16H 50/70; G06N 20/00; G06F 16/951
  USPC .................................................. 705/1.1–912
  See application file for complete search history.

(56) References Cited

U.S. PATENT DOCUMENTS

| | | | | |
|---|---|---|---|---|
| 7,925,557 B1* | 4/2011 | Ficery | | G06Q 40/02 705/35 |
| 8,364,569 B1 | 1/2013 | Lee, Jr. | | |
| 8,386,355 B1 | 2/2013 | Kajiwara et al. | | |
| 8,560,339 B2 | 10/2013 | Khan | | |
| 9,671,776 B1* | 6/2017 | Beard | | G05B 19/4063 |
| 10,394,776 B2 | 8/2019 | Khan | | |
| 10,572,496 B1* | 2/2020 | Frank | | G06F 3/0486 |
| 10,915,586 B2* | 2/2021 | Ulfelder, Jr. | | G06F 3/0482 |
| 10,922,633 B2* | 2/2021 | Ulizio | | G06Q 10/067 |
| 2003/0088492 A1* | 5/2003 | Damschroder | | G06Q 40/00 705/36 R |
| 2004/0015376 A1 | 1/2004 | Zhu et al. | | |
| 2008/0103804 A1* | 5/2008 | Latta | | G06Q 10/06 705/1.1 |
| 2010/0094685 A1 | 4/2010 | Young | | |
| 2012/0095802 A1 | 4/2012 | Van Cortlandt et al. | | |
| 2012/0197896 A1 | 8/2012 | Li et al. | | |
| 2013/0166476 A1* | 6/2013 | Samson | | G06Q 40/06 705/36 T |
| 2014/0156323 A1* | 6/2014 | Prieto | | G06Q 50/08 705/7.12 |
| 2015/0066577 A1* | 3/2015 | Christiansen | | G06Q 10/06 705/7.28 |
| 2015/0186815 A1 | 7/2015 | Han et al. | | |
| 2015/0206264 A1 | 7/2015 | Carrato et al. | | |
| 2015/0235143 A1* | 8/2015 | Eder | | G16H 50/50 706/12 |
| 2016/0034838 A1* | 2/2016 | Gembicki | | G06Q 10/06393 705/7.39 |
| 2016/0117774 A1* | 4/2016 | Bateman | | G06Q 40/06 705/36 R |
| 2016/0379326 A1* | 12/2016 | Chan-Gove | | H04L 63/1433 705/325 |
| 2018/0039567 A1* | 2/2018 | Rajagopalan | | G06F 11/3672 |
| 2019/0019119 A1 | 1/2019 | Lucas et al. | | |
| 2019/0139143 A1* | 5/2019 | Merker | | G06Q 10/06398 |
| 2019/0228490 A1 | 7/2019 | Prieto et al. | | |
| 2019/0236661 A1* | 8/2019 | Hogg | | H04L 63/1433 |
| 2019/0362427 A1* | 11/2019 | Chen | | G06F 40/30 |
| 2020/0143302 A1* | 5/2020 | Beard | | G06Q 10/0635 |
| 2021/0027379 A1* | 1/2021 | Zhu | | G06N 3/0472 |
| 2021/0037044 A1* | 2/2021 | Achanta | | G06N 20/00 |
| 2021/0092143 A1* | 3/2021 | Sbandi | | G06F 11/3612 |
| 2021/0110319 A1* | 4/2021 | Gourisetti | | G06Q 30/018 |
| 2021/0374469 A1* | 12/2021 | Molapo | | G06N 3/08 |

FOREIGN PATENT DOCUMENTS

| | | | |
|---|---|---|---|
| JP | 6564490 A | 8/2019 | |
| WO | 2017/125936 A1 | 7/2017 | |
| WO | 2018/222182 A1 | 12/2018 | |

OTHER PUBLICATIONS

J. Alindogan, Oct. 7, 2019, report on the World Health Organization's meeting in the Philippines after an outbreak of polio, 9 pages.
M. Barnish, "BMJ Open, How much evidence is there that political factors are related to population health outcomes? An internationally comparative systematic review", 10 pages, BMJ Open 2018;8:e020886. doi:10.1136/bmjopen-2017-020886.
J. Coumarianos, Barron's "Not All Sustainable Funds are Created Equal", Jan. 17, 2020, 6 pages.
J. Beaubien, npr, "The Philippines Is Fighting One of the World's Worst Measles Outbreaks", May 23, 2019, heard on Morning Edition, 34 pages.
C. Ngai et al., "For All the Talk About ESG Investing, Nobody Knows What it Means", Jan. 29, 2020, Finance, 6 pages.
D. Runde et al., "The Build Act Has Passed: What's Next?", Oct. 12, 2018, 17 pages, http://csis.org/search?f[0]=field_contributor%3a220>.
M. Chen et al., "The Global Pattern of Urbanization and Economic Growth: Evidence from the Last Three Decades", 15 pages, PLOS One 9(8): e103799. doi:10.1371/journal.pone.0103799, Key Laboratory of Regional Sustainable Development Modeling, Institute of Geographical Sciences and Natural Resources Research, Beijing, China, School of Geography, Beijing Normal University, Beijing, China.
P. Duarte et al., The World Economy, "Monetary policy, inequality and political instability", 21 pages, DOI: 10.1111/twec.12730, wileyonlinelibrary.com/journal/twec, World Econ. 2019;42:614-634.
D. Kovaleski, Homeland Preparedness News, "NTI Receives Grant to Create Global Health Security Index", Monday, Jul. 16, 2018, 4 pages.
Hurriyet Daily News, "Poverty is becoming a political problem", 7 pages, http://www.hurriyet.com.tr/veri-politikasi.
The National Academies Press, Washington, DC, www.nap.edu, A Consensus Study Report of The National Academies of Sciences, Engineering and Medicine, Committee on Improving the Quality of Health Care Globally, Board on Global Health, Board on Health Care Services, Health and Medicine Division, "Crossing the Global Quality Chasm Improving Health Care Worldwide", 398 pages, doi:https://doi.org/10.17226/25152.
Investment News, Feb. 15, 2020, "ESG's unsustainable irony: A lack of transparency", 2 pages.
Aljazeera, Sep. 20, 2019, Report on The Philippines launching a polio immunisation campaign and declared an outbreak in the country, 12 pages.
I. Kaloskampis, Data Science Campus, "Data Science for Public Good, Synthetic Data For Public Good", Feb. 21, 2019, 26 pages.
R. Katz et al., The Milbank Quarterly, vol. 89, No. 3, 2011, pp. 503-523, A Multidisciplinary Journal of Population Health and Health Policy, "Defining Health Diplomacy: Changing Demands in the Era of Globalization", George Washington University; Stimson Global Health Security Program.
G. Kell, "The Remarkable Rise of ESG", Jul. 11, 2018, 10 pages, LINFEN, Jun. 26, 2018.
S. Lansley, "Why Economic Inequality Leads to Collapse", The Observer, Saturday, Feb. 4, 2012, 5 pages.
G. Lopez-Casasnovas et al., "Health and Economic Growth: Findings and Policy Implications", the role of health on economic growth, 25 pages.
N. Madhav et al., "Pandemics: Risks, Impacts, and Mitigation", Chapter 17, Disease Control Priorities: Improving Health and Reducing Poverty, 31 pages.

(56) References Cited

OTHER PUBLICATIONS

B. Oppenheim et al., "Pandemics and the poor", Monday, Jun. 19, 2017, Blog by World Bank and Brookings Institution, www.worldbank.org, Sep. 2013, 4 pages.
Wikipedia, "Risk Assessment", 18 pages, https://en.wikipedia.org/wiki/Risk_Assessment, retrieved from: "https://en.wikipedia.org/w/index.php?title=Risk_assessment&oldid=1009594091".
Sandra Quinn"Health Inequalities and Infectious Disease Epidemics: A Challenge for Global Health Security", 12 pages, biosecurity and Bioterrorism: Biodefense Strategy, Practice, and Science, Sep. 2014, https://www.researchgate.net/publication/266153110.
Aika Rey, "Hontiveros says DOH's P10-billion budget cut an "attack on public Health"", Sep. 19, 2019, 11 pages.
Press Release,"The Rockefeller Foundation Announces $30 Mission Grant to the Adrienne Arsht Center for Resilience at the Atlantic Council", Apr. 1, 2019, 7 pages.
Ana P. Santos, "The Cure: Eliminating Dengue", Aljazeera Newsletter, Aug. 2019, 17 pages.
Interagency Coordination Group on Antimicrobial Resistance (IACG), "No Time to Wait: Securing the Future From Drug-Resistant Infections", Report to the Secretary-General of the United Nations, Apr. 2019, 28 pages.
Joanna Slater, "Dengue Cases are Surging Around the World. Some Blame a Changing Climate.", Oct. 4, 2019, 5 pages, The Washington Post, Mar. 14, 2021, https://www.washingtonpost.com/world/asia_pacific/dengue-cases-are...climate/2019/10/03/1a277532-e127-11e9-8fd3-d943b4ed57e0_story.html.
Leigh Stringer, "Mine Industry Scrambling to Cope wit Ebola Crises", Guardian Sustainable Business, Aug. 15, 2014, 4 pages.
Usaid, "Sustainable Urbanization for Global Progress and Security", urban@usaid.gov, 3 pages, Jul. 2017.
Justine Calma, "New Computer Model Predicts where Ebola Might Strike Next", The Verge, Oct. 2019, 3 pages.
Bryan Walsh, "The World is Not Ready for the Next Pandemic", Time Magazine, May 2017, 7 pages.
Tim Treadgold, "Ebola Provides Rio Tinto With a Second Reason to go Slow in Guinea", Nov. 2014, 3 pages.
Julia Belluz, "4 Reasons Disease Outbreaks are Erupting Around the World", Vox, May 2016, 12 pages.
World Health Organization, Western Pacific, Polio Outbreak in the Philippines, Sep. 2019, 21 pages.
Gilbert P. Felongco, "Filipinos Fight Dengue with Frogs and Fish", World Asia, Aug. 2019, 8 pages.
The World Bank, Press Release, Jun. 28, 2017, Emergency Financing Facility (PEF) launched, 4 pages.
The World Bank, Press Release, Oct. 23, 2018, Food-borne illnesses cost US $110 Billion per year in low- and middle-income countries, 4 pages.
The World Bank, "Understanding Poverty", Mar. 2020, 4 pages.
Ben Zimmer, "Infodemic: When Unreliable Information Spreads Far and Wide", 4 pages, Mar. 2021, https://www.wsj.com/articles/infodemic-when-unrealiable-information-spreads-far-and-wide-11583430244.
Orsetta Causa et al., "OECD Economics Department Working Papers No. 1180, Can Pro-growth Policies Lift all Boats? An Analysis Based on Household Disposable Income", https://dx.doi.org/10.1787/5jxrh8dh5wg7-en, 51 pages.
Rebecca Katz et al., "Global Health Security Agenda and the International Health Regulations: Moving Forward", 10 pages. Biosecurity and Bioterrorism: Biodefense Strategy, Practice and Science, vol. 12, No. 5, 2014, DOI:10.1089/bsp.2014.0038.
Jason Fernando, "Opportunity Cost," Investopedia, Dec. 27, 2020, https://www.investopedia.com/terms/o/opportunitycost.asp.
Centers for Disease Control and Prevention (CDC), "Cost-Effectiveness Analysis," Office of the Associate Director for Policy and Strategy, Mar. 5, 2021, https://www.cdc.gov/policy/polaris/economics/cost-effectiveness/index.html.
Economic Cost—Wikipedia, Dec. 22, 2020, https://en.wikipedia.org/wiki/Economic_cost.
Will Kenton, "Implicit Cost" definition, Investopedia, Oct. 25, 2020, https://www.investopedia.eom/terms/i/implicitcost.asp.
Adam Hayes, "Intangible Cost" definition, Investopedia, Jun. 30, 2021, https://www.investopedia.com/terms/i/intangiblecost.asp.
International Search Report and Written Opinion dated May 19, 2021 corresponding to International Patent Application No. PCT/US2021/020935.

* cited by examiner

RESILIENCE MEASUREMENT SYSTEM

CROSS-REFERENCE TO RELATED APPLICATION

This application claims the benefit of U.S. Provisional Patent Applications 62/985,842, filed Mar. 5, 2020, and 63/066,284, filed on Aug. 16, 2020, the contents of which are incorporated by reference herein in their entirety.

FIELD

Some example embodiments may generally relate to a resilience measurement system. For example, the resilience measurement system may assess various risk factors for decision-support.

BACKGROUND

Risk assessment may include identifying and analyzing potential (future) events that may negatively impact individuals, assets, and/or the environment. In addition, risk assessment may include making judgements while considering influencing factors estimating current vulnerability and/or informing mitigation strategies.

SUMMARY

According to a first embodiment, a method may include obtaining, by a resilience measurement system, information related to a set of resilience or public health-relevant risk factors and corresponding weights. The method may include calculating a score based on the set of resilience or public health-relevant risk factors and the corresponding weights. The method may include calculating a risk modifier based on the calculated score. The method may include performing an artificial intelligence or machine learning analysis. The method may include performing a cost analysis or scenario modeling based on a result of the artificial intelligence or machine learning analysis and performing a risk reduction, an opportunity maximization, or a cost reduction based on the cost analysis or the scenario modeling. The method may include performing an action based on a result of the cost analysis or the scenario modeling.

In a variant, the obtaining of the information may further include obtaining the information by querying the information, by receiving a push of the information, by scraping a website, or via a user interface associated with the resilience measurement system. In a variant, the calculating of the score may further include calculating the score by multiplying the corresponding weights by scores for the set of resilience or public health-relevant risk factors and processing the scores for the set of resilience or public health-relevant risk factors. In a variant, the set of resilience or public health-relevant risk factors may include at least one of: outbreak risk factors, climate and environmental risk factors, human health risk factors, country profile risk factors, political risk factors, institutional integrity risk factors, operational risk factors, one health risk factors, or financial risk factors.

In a variant, the method may further include determining an index for estimated lost gross domestic product or economic costs based on the resilience or public health-relevant risk factors. In a variant, the performing of the action may further include outputting, to an output device, the result of the cost analysis or the scenario modeling for storage or display. In a variant, the performing of the action may further include communicating with a server device to rebalance an investment portfolio or rate stocks or other assets based on the result of the result of the cost analysis or the scenario modeling.

In a variant, the calculation of the risk modifier may further include processing a value by the score. In a variant, the score may be a total score based on scores for the set of resilience or public health-relevant risk factors. In a variant, the performing the artificial intelligence or machine learning analysis may further include performing the artificial intelligence or machine learning analysis using at least one of: pattern recognition, decision science, an artificial intelligence or machine learning model, data scraping, a risk reduction process, an opportunity maximization, or the scenario modeling. In a variant, the method may further include determining a rating for a security, currency, or an asset based on the risk modifier.

In a variant, the performing the cost analysis may further include perform the cost analysis of at least one of: one or more economic costs, one or more financial costs, one or more opportunity costs, a return on investment optimization, value for money, or opportunity identification. In a variant, the performing the action may further include generating a recommendation related to an investment, modification to business operations, or strategic resource allocation for maximum benefit, efficacy, or return on investment, and outputting the recommendation for display via an output device. In a variant, the calculating the score may include calculating scores for sub-risk factors of each of the set of resilience or public health-relevant risk factors, calculating scores for each of the set of resilience or public health-relevant risk factors based on the scores for the sub-risk factors, and/or calculating the score for the set of resilience or public health-relevant risk factors based on the scores for each of the set of resilience or public health-relevant risk factors.

In a variant, the method may further include recommending a risk reduction strategy or identifying an opportunity. In a variant, the obtaining the information may include obtaining the information by querying the information, by receiving a push of the information, by scraping a website, or via a user interface associated with the resilience measurement system. In a variant, the calculating the score may include calculating the score by multiplying the corresponding weights by scores for the set of resilience or public health-relevant risk factors and processing the scores for the set of resilience or public health-relevant risk factors. In a variant, the method may further include performing statistical modeling or scenario modeling to assess a likelihood of an event occurring within a given time period.

In a variant, the calculating the risk modifier may include processing a value by the score. In a variant, the score may be a total score based on scores for the set of resilience or public health-relevant risk factors. In a variant, the performing the artificial intelligence or machine learning analysis may include performing the artificial intelligence or machine learning analysis using at least one of: pattern recognition, decision science, an artificial intelligence or machine learning model, data scraping, a risk reduction process, a cost reduction process, an opportunity maximization, the scenario modeling, or one or more types of simulations to calculate statistical likelihoods. In a variant, the performing the cost analysis may further include performing the cost analysis of at least one of: one or more economic costs, one or more financial costs, one or more opportunity costs, a return on investment optimization, an opportunity maximization, or a risk minimization. In a variant, the performing the artificial intelligence or machine learning model may include performing a Monte Carlo simulation.

A second embodiment may be directed to an apparatus including at least one processor and at least one memory comprising computer program code. The at least one memory and computer program code may be configured, with the at least one processor, to cause the apparatus at least to perform the method according to the first embodiment, or any of the variants discussed above.

A third embodiment may be directed to an apparatus that may include circuitry configured to cause the apparatus to perform the method according to the first embodiment, or any of the variants discussed above.

A fourth embodiment may be directed to an apparatus that may include means for performing the method according to the first embodiment, or any of the variants discussed above. Examples of the means may include one or more processors, memory, and/or computer program codes for causing the performance of the operation.

A fifth embodiment may be directed to a computer readable medium comprising program instructions stored thereon for causing an apparatus to perform at least the method according to the first embodiment, or any of the variants discussed above.

A sixth embodiment may be directed to a computer program product encoding instructions for causing an apparatus to perform at least the method according to the first embodiment, or any of the variants discussed above.

BRIEF DESCRIPTION OF THE DRAWINGS

For proper understanding of example embodiments, reference should be made to the accompanying drawings, wherein.

DETAILED DESCRIPTION

Figure 1:
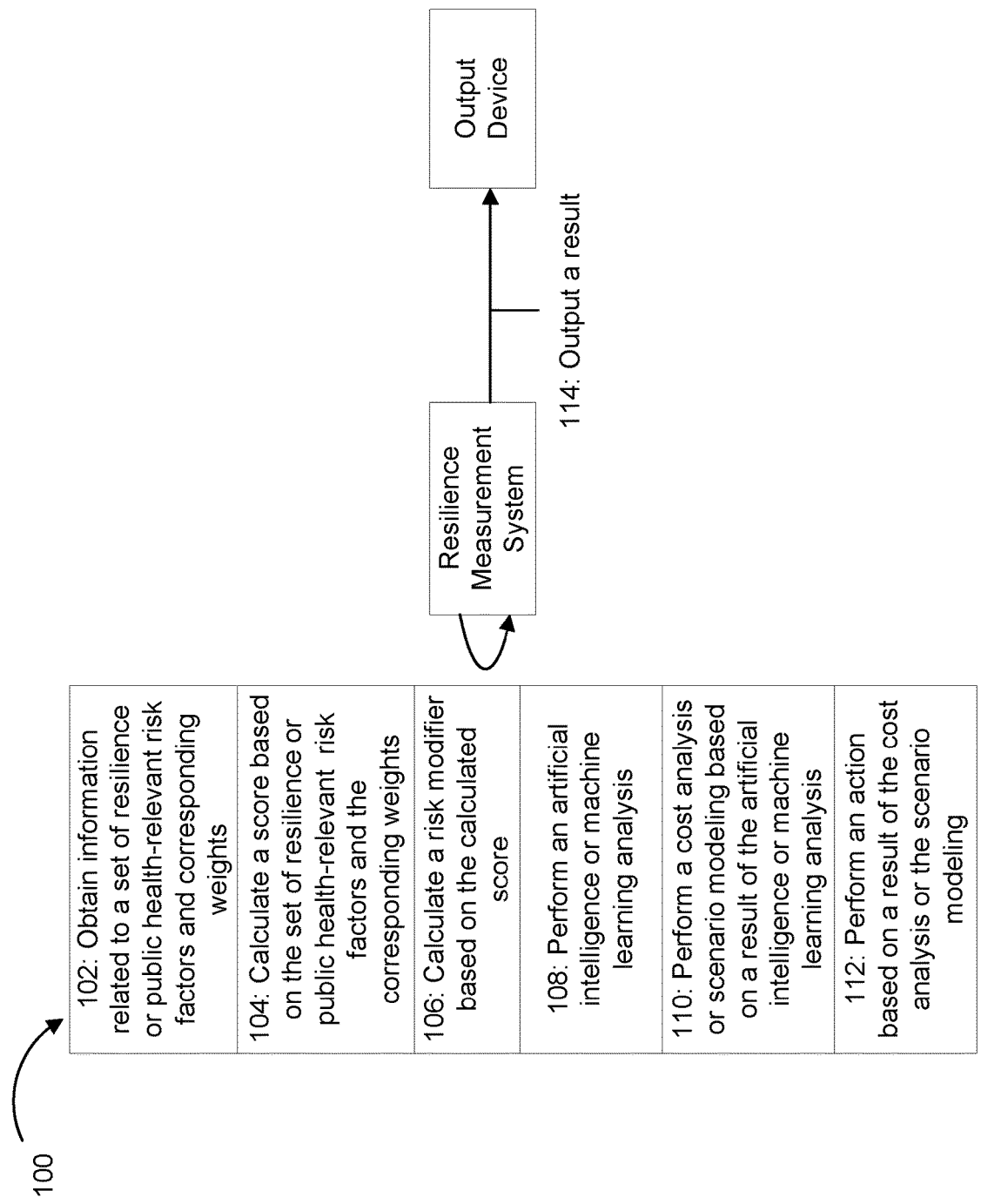
FIG. 1 illustrates an example of operations of a resilience measurement system, according to some embodiments.

It will be readily understood that the components of certain example embodiments, as generally described and illustrated in the figures herein, may be arranged and designed in a wide variety of different configurations. Thus, the following detailed description of some example embodiments of systems, methods, apparatuses, and computer program products for operations of a resilience measurement system is not intended to limit the scope of certain embodiments but is representative of selected example embodiments.

The features, structures, or characteristics of example embodiments described throughout this specification may be combined in any suitable manner in one or more example embodiments. For example, the usage of the phrases "certain embodiments," "some embodiments," or other similar language, throughout this specification refers to the fact that a particular feature, structure, or characteristic described in connection with an embodiment may be included in at least one embodiment. Thus, appearances of the phrases "in certain embodiments," "in some embodiments," "in other embodiments," or other similar language, throughout this specification do not necessarily all refer to the same group of embodiments, and the described features, structures, or characteristics may be combined in any suitable manner in one or more example embodiments. In addition, the phrase "set of" refers to a set that includes one or more of the referenced set members. As such, the phrases "set of," "one or more of," and "at least one of," or equivalent phrases, may be used interchangeably. Further, "or" is intended to mean "and/or," unless explicitly stated otherwise.

Additionally, if desired, the different functions or operations discussed below may be performed in a different order and/or concurrently with each other. Furthermore, if desired, one or more of the described functions or operations may be optional or may be combined. As such, the following description should be considered as merely illustrative of the principles and teachings of certain example embodiments, and not in limitation thereof.

Stakeholders and others may rely on risk analyses to identify or manage potential problems that can undermine certain initiatives or projects, including business initiatives, such as investment decisions. As issues like climate change, inequality, and urbanization prompt the resurgence and spread of disease, political, and other risk models may need to incorporate these or similar risks to give investors a clearer view of the evolving landscape. Political factors may be related to population health outcomes and globalization may have a negative impact on population health, indicating that current investment models lack an important sustainability component.

The stakes may be high for stakeholders or others, especially when it comes to risks resulting in health costs, e.g., related to pandemic potential. Some estimates conclude that a pandemic flu may cost the world over $4 trillion (USD) and a moderately severe to severe flu may cost approximately $570 billion (USD). For example, the International Monetary Fund in October 2020 estimated the final global bill for lost productivity resulting from SARS-CoV-2/COVID-19, the COVID-19 pandemic, would total almost $28 trillion (USD), while other events with human health consequences, like climate change, are estimated to displace 20 million people each year. Chronic health issues also may have significant consequences as well with cardiovascular disease costing the United States $219 billion (USD) from 2014-2015 according to the Center for Disease Control and Prevention (CDC). As the COVID-19 pandemic has demonstrated, the world is not prepared for a pandemic or its subsequent shock events, and is not able to manage the factors, which exacerbate shock events, including pandemics. Clients face huge economic exposure if current risk assessments (e.g., assessments of political risk, actuarial risks, etc.) do not anticipate the needs of clients in this capacity. Shock events are inevitable, and resilience decreases associated cost and reduces financial exposure. A comprehensive model that incorporates political risk and disease forecasting, among other health indicators, can help businesses or other organizations make the right decisions in an increasingly volatile world and can inform strategic resource allocation.

Risk assessments at large do not adequately incorporate public health data to sufficiently measure factors that can result in instability. More importantly, it may not consider the bidirectional relationship between public health and risk, or how health indicators can help measure risk more clearly, primarily as it relates to the impact on capital (e.g., human capital, environmental capital, financial capital, etc.), which may be a major driver of the global economy and of individual economies around the world. Political decisions and policies related to factors associated with social determinants of health can have impacts on human capital, e.g., health access and the ability for people to thrive, which may affect productivity and growth. Social determinants of health can influence the health of populations. Social determinants of health, including income and social status; social support networks; education; employment/working conditions; social environments; physical environments; personal health practices and coping skills; healthy child development; gender; and culture. These circumstances may be shaped by the distribution of money, power, and/or resources at global, national, and local levels and can impact realized human capital because of the ability of one or more of these factors to impact health outcomes, quality of life through resultant events like stunting, loss of life, opportunity loss or other events which can impact productivity, and in the aggregate, create instability at the population level yielding events including uprisings, especially when considering, for example, the health-poverty trap, which may result in losses in growth.

Resilience, on the other hand, may be the ability of an individual, community, population, infrastructure, government, or other entity to absorb, adapt, anticipate and transform when exposed to external threats—and/or to forecast shocks that bring about new challenges and opportunities—and still retain control over its remit and pursuit of its primary objectives and functions.

This may leave a major gap in existing political risk and other widely used analyses because of public health's impact on stability at the macro and micro level. Key public health indicators may include inequality and urbanization, which may impact a country or a population's stability, gross domestic product (GDP), and the chance of outbreaks with pandemic potential.

Governments and political entities may be starting to appreciate this connection. In recent years, for example, they have started to invest heavily in health and vaccine diplomacy and surveillance programs. For instance, certain organizations have called for urgent action against antimicrobial resistance and politicians may be becoming increasingly involved in domestic and global health concerns.

Scientific and public health literacy may be low, depending on the context. This may contribute to the rise of "infodemics" that are often observed when outbreaks happen. However, there may be widespread persistence of incorrect information as is observed with other disinformation campaigns, including the anti-vaccination movement reflecting a larger deterioration in institutions.

As volatility increases, risk models may have to weigh their impact and the ability for countries, companies, and stakeholders to operate within the constraints created by it. One of these measures may include human resilience and productivity. These two factors may be of particular importance because of their primary and secondary impacts on capital, including human capital. Incorporating human development and outbreak risk and response into existing risk models can make currently utilized service bundles more comprehensive.

Resilience and risk can be determined using social determinants of health, public health, one health, and other health relevant metrics. "One health" approach may refer to the intersection of human, animal, and environmental health, or other types of risk factors, such as, those defined, for example, by the One Health Commission, the Center for Disease Control and Prevention, the World Health Organization or other national, regional and international health organizations or professionals. For example, One health may apply a coordinated, collaborative, multidisciplinary and cross-sectoral approach to assess and address potential or existing risks that originate at the animal-human-ecosystems interface through the design and implementation of programs, policies, legislation and research in which multiple sectors communicate and work together to achieve better public health outcomes. In some alternatives, the One health approach may be utilized at local, regional, national and global levels for work related food safety, the control of zoonoses (diseases that can spread between animals and humans, such as flu, rabies and Rift Valley Fever), and combatting antibiotic resistance (when bacteria change after being exposed to antibiotics and become more difficult to treat). Because of the multifaceted nature of shock events, creating a risk value based on the determinants may allow for a single measurable indicator that can translate across country systems and issues.

Some embodiments described herein may provide for a resilience measurement system. For example, the resilience measurement system may receive data from multiple sources, and may measure resiliency based on this data, such as the ability of a population or geographic area (e.g., a country) to withstand emerging threats posed by climate, health, globalization, and risks to human development. The resilience measurement system may calculate one or more scores indicating, e.g., risk, need for program adjustment, or need for policy change and investment, depending on the client or the project. To perform such operations, the resilience measurement system may process index scores for different categories of threats to average the index scores for different categories of threats with different weights based on the specific needs of a particular scenario or requirement, which may then be averaged, in some cases, to compute one or more total scores. The total scores may be used by the resilience measurement system for additional analysis, to perform actions, and/or the like and may provide inputs for a decision support system.

The resilience measurement system may perform pattern recognition through data collection and aggregation over time to identify real-time changes to trends and provide early alert for events. Additionally, or alternatively, the resilience measurement system may perform decision-making support using artificial intelligence (AI) and/or machine learning (ML) analysis and/or decision science to test different interventions through data application and scenario testing. Additionally, or alternatively, the resilience measurement system may perform data collection through data scraping and other mechanisms for the collection of structured and unstructured data.

Furthermore, the resilience measurement system may perform processing to generate a risk metric that itemizes risk factors that may impact human capital and efficiency, and things that it impacts or is impacted by. Through these operations, the resilience measurement system may support decision-making for mitigating risk and opportunities for investment and growth. The decision-making support may be used to weigh risk and opportunities in the short term (e.g., 1-2 years), the medium term (e.g., 2-5 years), and the long term (e.g., 7+ years) through consideration of both financial (e.g., money) costs and economic (e.g., money, development, health, etc.) costs. Alternatively, the decision-making support may be used to weigh risk and opportunities for a customized time period that is desired by a particular scenario or requirement.

In this way, the resilience measurement system may provide a model that can create a more comprehensive service bundle for decision support or program analysis in a rapidly expanding market. Additionally, the resilience measurement system can provide information and/or perform actions that can help assess risks of certain businesses, business sectors, and associated assets, including stocks by building in risk capacity and understanding for these sectors. This can facilitate organizations and/or individuals to prepare for and/or prevent high cost scenarios, which may disrupt operations of the organizations and/or individuals. This information can also be transmitted to consumers of stocks and allow them to make decisions based on their personal values, as with environmental, social, and governance (ESG) organizations but using this method to, thus, create a health, environmental, social, and governance (HESG) organization, such as a Health ESG fund.

Certain embodiments described herein may be applicable to scenarios other than pandemic risk. For instance, the resilience measurement system may analyze capital (K) or human capital. The resilience measurement system may perform computations to increase and optimize (K) that may result in an increase in overall projected global output that increases the amount of gross domestic product (GDP) the world can collectively produce, thus, facilitating lifting of people out of poverty, improving livelihoods of populations, and improving health of populations.

In certain embodiments, the resilience measurement system may incorporate resilience into political risk models because it can provide for improved guidance and strategic decision-making for companies operating in increasingly challenging settings. In addition, this may provide for improved guidance and strategic decision-making for governmental organizations wanting to maintain and increase the public health and resilience of their populations and incentivize international investment and aid into their countries, and for non-governmental organizations (NGOs) and foreign government planning to execute global health and/or resilience activities.

In this way, the resilience measurement system may help governments, private entities, and NGOs better plan for new investments, and protect their existing investments, by presenting a comprehensive risk assessment that includes, e.g., consideration of political risk, public health risk, one health risk, disease risk, and resiliency through processes that measure, e.g., human and/or country resiliency versus shock risk. Based on the factors, the resilience measurement system may provide information that decision-makers can use to identify their weaknesses, more easily identify subcategories of weaknesses, and/or make targeted preventative or reactive decisions to mitigate cost or damage.

In addition, in this way, the resilience measurement system may itemize opportunity and risk for strategic resource allocation, risk reduction, and opportunity development based on resilience or public health-relevant risk factors (e.g., optimization of human capital). For example, the resilience measurement system may perform operations that support evidence-based decision-making for strategic resource allocation and risk reduction through artificial intelligence (AI) and/or machine learning (ML) analysis, decision science, and/or the like.

Resilience or public health-relevant risk factors may include social determinants of health, infrastructure, nutrition, climate and environment, and political conditions, one health, which may influence a person's ability to thrive physically and mentally. As such, certain embodiments may take into consideration factors not typically associated with direct health outcomes including health policies, political stability, infrastructure development, supply chain capacity, educational attainment, severity of climate and environmental risk, or infectious disease outbreaks and capacity and dynamics for control. Because humans stand at the center of various aspects of the economy, global development, and risk, certain embodiments may itemize health risks, and may provide analysis that informs decision-making on a broad variety of issues through a human-centered perspective of risk.

FIG. 1 illustrates an example 100 of operations of a resilience measurement system, according to some embodiments. As illustrated in FIG. 1, the example 100 includes a resilience measurement system and an output device. The resilience measurement system may include one or more computing devices, such as one or more servers (e.g., in a cloud deployment or in a data center), one or more personal computers, and/or the like. The output device may include one or more computing devices, such as one or more desktop or laptop computers, one or more tablets, one or more mobile phones, etc.

As illustrated at 102, the resilience measurement system may obtain information related to a set of resilience or public health-relevant risk factors and corresponding weights. For example, the resilience measurement system may obtain the information from one or more computing device that store the information (e.g., may obtain the information periodically, according to a schedule, when the information has changed, etc.). In some embodiments, the resilience measurement system may obtain the information related to the set of resilience or public health-relevant risk factors by sending a request or a query for the information, may receive a push of the information, may use a web crawler to scrape information (e.g., structured or unstructured data) or program code associated with a website, may receive the information via a user interface, and/or the like. The information related to the resilience or public health-relevant risk factors may be associated with a corresponding index and may include a value within a range of values. For example, the value may indicate a severity of the risk factor. In some instances, these factors may be assigned a value (e.g., a monetary value) to help inform subsequent decision making when the objectives are to understand the cost of risks, avoid financial loss, or understand the cost and/or benefit of specific interventions.

The resilience measurement system may obtain the information related to the corresponding weights via a user interface associated with the resilience measurement system, using an artificial intelligence or machine learning model (e.g., the artificial intelligence or machine learning model may process information related to an organization or an individual for which analysis is being performed to determine weights to be applied based on characteristics of the organization or the individual), and/or the like. The weight may include a value that indicates a priority or an importance of a resilience or public health-relevant risk factor related to one or more other risk factors. In some embodiments, the information obtained at 102 may be obtained from a platform associated with the resilience measurement system or an owner of the resilience measurement system, or from a platform associated with another party.

In certain embodiments, after obtaining the information, the resilience measurement system may perform statistical modeling or scenario modeling (e.g., using a generative adversarial network (GAN) or another type of deep neural network) to assess a likelihood or statistical probability of an event occurring within a given time period. For example, the resilience measurement system may perform data scraping to obtain scenarios (or the scenarios may be specified by a user of the resilience measurement system) and processing data related to the scenarios (e.g., associated risk or likelihoods). As a specific example, a company may be considering laying off employees, and the resilience measurement system may use data scraping to identify that switching employees from full-time to part-time could a solution and may identify risks associated with this course of action. As another specific example, the scenario modeling may utilize pattern recognition, e.g., if the resilience measurement system updates data in real time, or near real-time, the resilience measurement system may determine irregular patterns in it's refreshed data sets, such as a sudden increase in pneumonia outside of the norm for that time of year, which might indicate an outbreak.

In certain embodiments, the resilience measurement system may obtain the information by using an AI and/or ML model to generate the information. For example, the resilience measurement system may populate a database (or other data structure) with data created through life-like simulated scenarios performed by the AI and/or ML model (e.g., a generative adversarial network (GAN) or another type of deep neural network).

As illustrated at 104, the resilience measurement system may calculate a score based on the set of resilience or public health-relevant risk factors and the corresponding weights. For example, the resilience measurement system may multiply the weight by the value of the risk factor, may apply a formula to the weight and the value of the risk factor, and/or the like. The resilience measurement system may calculate a score for each resilience or public health-relevant risk factor, may aggregate scores for resilience or public health-relevant risk factors into various categories of resilience or public health-relevant risk factors, and/or the like. In some embodiments, the resilience measurement system may calculate a total score for multiple resilience or public health-relevant risk factors. For example, the resilience measurement system may add, subtract, multiply, or divide the scores for the resilience or public health-relevant risk factors, may apply a formula to the resilience or public health-relevant risk factors, and/or the like. The resilience measurement system may use data collected at 102 or determined at 104, in connection with an AI or a ML model, to perform Monte Carlo simulations, or the like to assess the likelihood of events occurring within a given time period based on an assessed risk.

As illustrated at 106, the resilience measurement system may calculate a risk modifier based on the calculated score. For example, the resilience measurement system may divide a value by the total score determined at 104, may multiply the total score by a value, may apply a formula to the total score, and/or the like.

A risk modifier may include a value generated by aggregating risk metrics to create a single value which can be multiplied or divided (or processed through some other operation) to try to illustrate an accurate risk potential of a given scenario. For example, in the case of an epidemiological chart, which charts the size of an outbreak, the risk modifier may provide a more accurate size of the outbreak based on the given location and other risk factors, which could exacerbate an outbreak. Continuing with this example, a risk modifier may indicate, among other information, where preventive strategies are likely to be adopted and indicate when they are not, thus informing an iterative real time response in appropriately targeted areas. Another example relates to assessment of company operational risk where a company operates in an environment or when its operations pose specific risks to human or community health. A risk modifier can be incorporated into, e.g., existing risk assessments of company business operations, its stocks, and relevant ESG funds. In the event a company had, e.g., a AAA rating (highest rating) but had severe risk due to weather, the risk modifier can be pegged to the AAA rating either first through conversion to a corresponding letter or to the underlying values which read out as the letter rating system to produce, for instance, a BB rating (a lower rating than AAA), thereby modifying the AAA rating to reflect the operational risk of the company. Because certain embodiments may include building risk modifiers over set time frames using projections, certain embodiments can allow for scoring of an asset or company in question over set time frames. In the event the risk was lower in the short term but higher in the long term, for example, the modifier can recommend changing the AAA rating to AA in the short term but to BB in the medium term and B in the long term. Additionally, because certain embodiments may include itemizing risk components, the score can also inform stakeholders of ways in which risk can be mitigated or what health promotion strategies and opportunities may be used to increase their ratings.

As illustrated at 108, the resilience measurement system may perform an artificial intelligence or machine learning analysis. For example, the resilience measurement system may perform the artificial intelligence or machine learning analysis by performing scenario modeling and testing to identify various scenario outcomes based on the risk modifier, based on baseline data for a scenario, and/or the like. The artificial intelligence or machine learning analysis may use a model that can be trained to process baseline data for a scenario and a risk modifier. Output from the artificial intelligence or the machine learning analysis may include various outcomes for the scenarios and probabilities or likelihoods for the various outcomes. In certain embodiments, cost may be a factor or an objective in the artificial intelligence or machine learning analysis. The artificial intelligence or machine learning analysis may utilize pattern recognition, data science, an artificial intelligence or machine learning model, data scraping, a risk reduction algorithm, and/or the like.

As another example, a risk modifier may be processed using a statistical model to calculate probabilities and/or likelihoods of an adverse event. In this case, the weights associated with the risk modifier may indicate which adverse event may occur (e.g., pandemic versus flood). Processing using the statistical model may be performed in connection with the operations at 104 above.

As illustrated at 110, the resilience measurement system may perform a cost analysis or scenario modeling based on a result of the artificial intelligence or machine learning analysis. For example, the resilience measurement system may utilize a trained model to perform an economic analysis, a financial cost analysis, a return on investment (ROI) analysis, and/or the like for an investment by processing data related to the investment and an outcome from the artificial intelligence or machine learning model to determine a financial impact to an investment. Continuing with the previous example, the resilience measurement system may determine a predicted value of an investment at a time in the future, a present value of the investment, and/or the like.

As illustrated at 112, the resilience measurement system may perform an action based on a result of the cost analysis or the scenario modeling. For example, the resilience measurement system may output a result of the cost analysis, at 114, via a display of the output device, may store the result, and/or the like. In certain embodiments, the resilience measurement system may generate a report or other output format that includes a result of the cost analysis and may output the report, may communicate with a server to rebalance a portfolio of investments based on the result (e.g., by sending an instruction to change a percentage of the portfolio of certain investments by selling or buying additional instances of the asset), may generate a recommendation related to an investment, may send a message to the output device if the cost analysis indicates that a value of an investment is below a threshold, and/or the like or recommend changes to business operations.

As described above, FIG. 1 is provided as an example. Other examples are possible, according to some embodiments.

Figure 2:
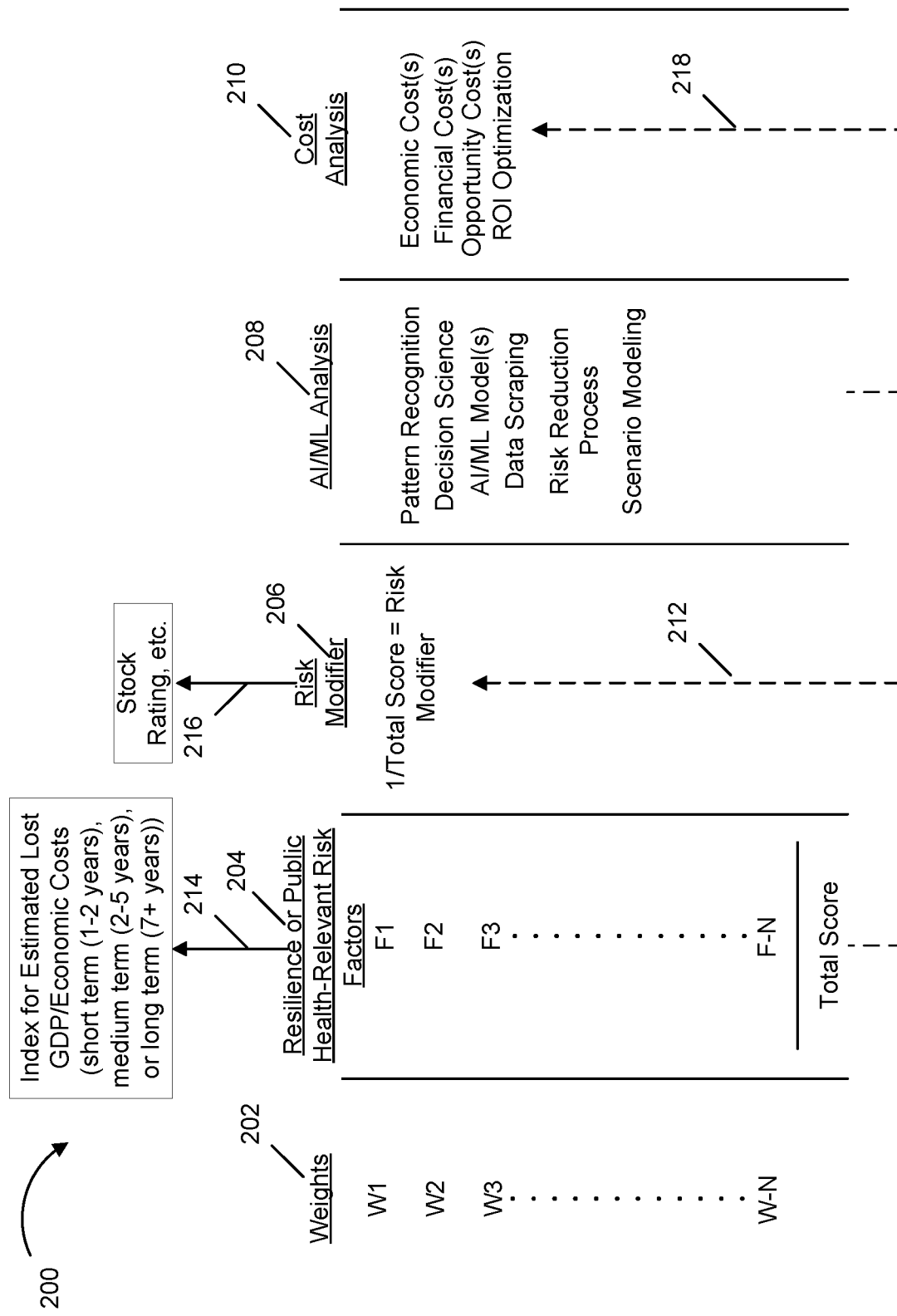
FIG. 2 illustrates another example of operations of the resilience measurement system, according to some embodiments.

FIG. 2 illustrates another example 200 of operations of the resilience measurement system, according to some embodiments. As illustrated at 202, the resilience measurement system may obtain weights W1 through W-N. The weights may correspond to risk factors F1 through F-N at 204, which the resilience measurement system may also obtain. The risk modifier that the resilience measurement system calculates is illustrated at 206, the causal artificial intelligence or machine learning analysis that the resilience measurement system may perform is illustrated at 208, and the cost analysis that the resilience measurement system may perform is illustrated at 210. As illustrated at 212, the total score that the resilience measurement system calculates from the resilience or public health-relevant risk factors and weights may be used to determine the risk modifier.

As illustrated at 214, the resilience or public health-relevant risk factors may be used to determine an index for estimated lost GDP and/or economic costs (e.g., over a short term (e.g., 1-2 years), a medium term (e.g., 2-5 years), and a long term (e.g., 7+ years)). For example, the resilience measurement system may calculate an adjusted index based on the resilience or public health-relevant risk factors. Continuing with the previous example, risk factors may be associated with threats to, e.g., human capital and productivity, and the resilience measurement system may aggregate risk factors into one or more categories. The resilience measurement system may determine values for the categories based on the values of the risk factors, and may determine a value of an index based on the values for the categories. As illustrated at 216, the calculated risk modifier may be used to determine a stock rating or a rating for another security or asset. For example, the resilience measurement system may rate stocks (or other assets or securities) based on the risk modifier including commodities and companies based on risk associated with the stocks. The risk modifier may be used to determine a rating for another type of product (e.g., another type of asset, a good, a service, etc.). As illustrated at 218, output from the artificial intelligence or machine learning analysis may be incorporated into the cost analysis that the resilience measurement system performs.

As indicated above, FIG. 2 is provided as an example. Other examples are possible, according to some embodiments. For example, in other embodiments, the resilience measurement system may provide recommendations to an individual, rather than an organization, regarding how to improve, e.g., their health and/or manage personal health risks (independent of a pandemic or another shock event).

Figure 3A:
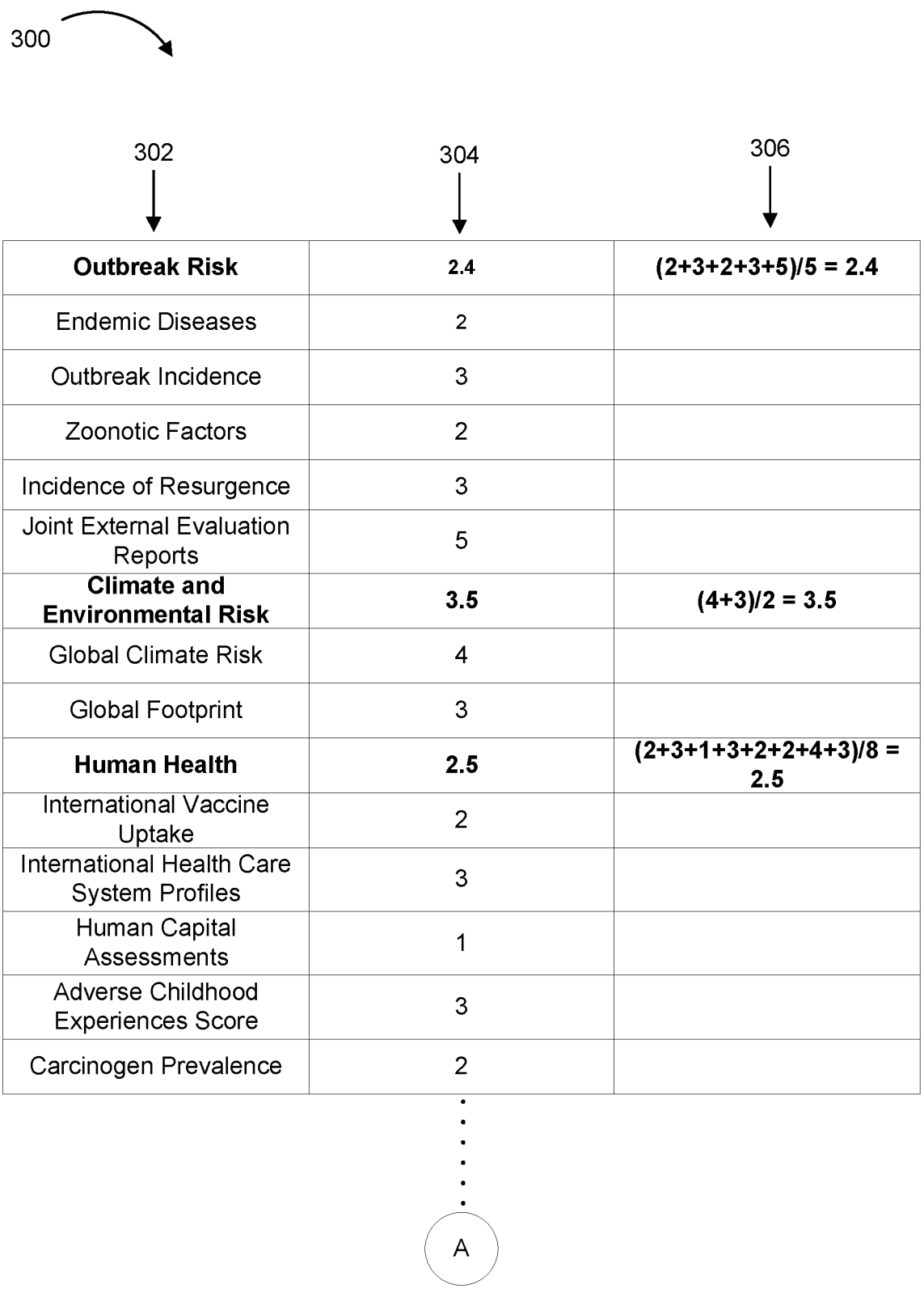
FIGS. 3a and 3b illustrate an example of score calculation, according to some embodiments.
Figure 3B:
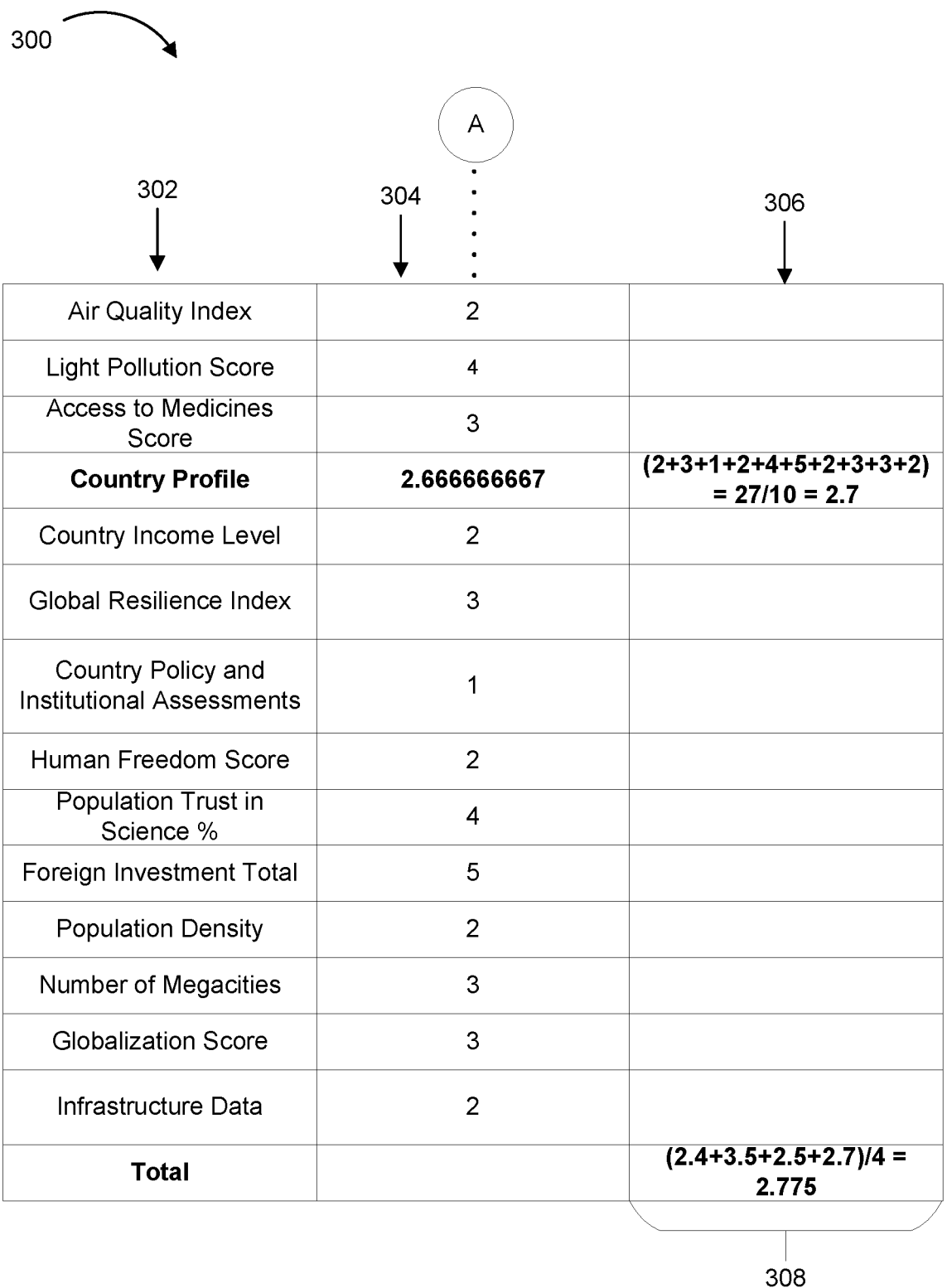

FIGS. 3a and 3b illustrate an example of score calculation, according to some embodiments. In particular, FIGS. 3a and 3b illustrate, at 302, resilience or public health-relevant risk factors for which the resilience measurement system may obtain information. The risk factors may include various categories of resilience and resilience or public health-relevant risk factors, such as outbreak risk (e.g., risk of disease outbreak in a geographic region or to a population), climate and environmental risk factors (e.g., risk of negative impacts due to climate and environmental changes to a geographic region or to a population), human health risk factors (e.g., risk factors related to the health of a population), country profile risk factors (e.g., risk factors specific to a geographic area), and/or the like. As further illustrated at 302, the resilience or public health-relevant risk factors may be associated with sub-risk factors, or sub-categories of information. For example, the outbreak risk factor may be associated with endemic diseases risk factors, outbreak incidence risk factors, etc. as sub-risk factors.

As illustrated at 304 of FIGS. 3a and 3b, each of the resilience or public health-relevant risk factors may be associated with a score that indicates a severity of the risk factors. For example, the outbreak risk factor may be associated with a score of 2.4, and each of the sub-risk factors may be associated with corresponding scores (e.g., the endemic diseases sub-risk factor is associated with a score of 2, the outbreak incidence risk factor is associated with a score of 3, etc.). As illustrated at 306 of FIGS. 3a and 3b, the resilience measurement system may calculate the scores for the resilience or public health-relevant risk factors based on the scores for the sub-risk factors. For example, the scores for the sub-categories of risk factors may be summed and the resilience measurement system may calculate an average score for the sub-risk factors by dividing the sum by the number of sub-risk factors. As a specific example, for the outbreak disease risk factor, the scores for the sub-risk factors of endemic diseases, outbreak incidence, etc. may be summed and divided by 5, since there are 5 sub-risk factors associated with the outbreak risk factor resulting in a score of 2.4. As illustrated at 308 in FIG. 3b, the resilience measurement system may calculate a total score for the various resilience or public health-relevant risk factors. For example, the resilience measurement system may sum and average scores for the various resilience or public health-relevant risk factors (e.g., in the example 300 the total score is illustrated as 2.775).

In certain embodiments, the resilience measurement system may determine whether the total score (or any of the other calculated scores) satisfies a threshold, may evaluate an investment based on the score(s) (e.g., may identify the value of risks to the investment based on the score(s)), and/or the like, as described elsewhere herein. Although the example 300 includes the resilience measurement system computing an average of the scores for sub-risk factors, other computations, such as applying a formula, can be used. In addition, in the example 300, the different resilience or public health-relevant risk factors, and the sub-risk factors, may be weighted equally, but different weights can be applied in other examples.

In this way, the resilience measurement system may measure resiliency, which may include the ability of a population and/or country to withstand emerging threats posed by climate, health, globalization, and human development risk factors. The resilience measurement system may be configurable, or may automatically reconfigure operations (e.g., through use of a machine learning model to determine the configurations), to reflect client needs and overall risks. For example, the resilience measurement system may modify resilience or public health-relevant risk factors (or sub-risk factors) used in the analysis, may modify weights for the risk factors, and/or the like based on the client, the analysis being performed, etc. The resilience measurement system may weight different modifiers based on, e.g., industry, user/client objectives for analysis, country-specific health considerations, and investments. As an example, the resilience measurement system may produce values from 0 to 5, indicating, e.g., risk, need for program adjustment, or need for policy change and investment depending on the client and the project. Because the resilience measurement system may use indexes and reports with different valuation schemes corresponding to the sub-risk factors, analysis of each of the index scores may be performed by the resilience measurement system (e.g., using a machine learning model) and then given a score from 0-5. These scores for the sub-risk factors may then be averaged, or averaged with different weights, based on the specific needs of clients to determine a score for the various resilience or public health-relevant risk factors. These scores may then be averaged together, or given a weighted average, depending on client needs, for a total score. While a scenario may be associated with a total score, the total score may be weighted against one or more driving factors. Additional analysis may be performed to better advise and inform the client.

Furthermore, because the resilience measurement system of certain embodiments may provide resilience modeling, the resilience measurement system may incorporate health and scientific information, through the use of artificial intelligence or machine learning modeling, into risk analysis in a manner not possible through conventional analysis. In addition, the resilience measurement system may process information related to financial and economic costs of an outbreak and can facilitate market resilience analyses. Furthermore, the resilience measurement system may provide indications of resilience that are not otherwise possible.

As described above, FIGS. 3a and 3b are provided as examples. Other examples are possible, according to some embodiments.

As explained elsewhere herein, certain embodiments may obtain information from indices and/or reports. For example, these indices and/or reports may be publicly available (e.g., published on a website or available through subscription to a data stream) and may provide relevant analyses by experts in their respective fields. In this way, the resilience measurement system may utilize information for meaningful verification and corroboration at a low cost.

In addition, the resilience measurement system may calculate and publish a public-facing index based on results of analyses performed by the resilience measurement system. For example, the resilience measurement system may push information related to the index to devices or accounts that have subscribed to such information, may update a website hosted on a server with the information related to the index, and/or the like. This index may rank investment risk per country based on a combination of disease forecasting, surveillance models with traditional risk analysis factors, such as development, freedom, and access to education, and/or based on other factors.

The resilience measurement system can adjust rating and risk models based on results of the analyses the resilience measurement system performs. For example, the scores can be used in financial markets along with environmental, social, and governance (ESG) Funds. Adding the score to ESG funds can offer countries, businesses, investors, stakeholders, and stockholders a more comprehensive understanding of how businesses and their operations impact the environments in which they exist, their sustainability weaknesses, and the health and resilience risk they both pose and face through the incorporation of a human centered approach to risk. As such, relevant entities can make important decisions for both proactive prevention and protection to promote more sustainable investment, which may emphasize human health and resilience in the long-term. This can provide for using the rating scale to create an ESG, which may include consideration of relevant resilience and public health risks of employees, industry, and countries.

Emphasis on certain embodiments of the resilience measurement system may give the company the ability to collect data and trends over time through tracking the input values via platforms like social media, journal publications, country surveys and censuses, reports from international actors and multilateral institutions, think-tanks, and others. This may provide for an evidence-based analysis that can help to make scientific topics accessible to the lay reader. The resilience measurement system can be public facing and, by serving as an evidence-based lifestyle publication, can communicate important emerging scientific information about, e.g., health. The resilience measurement system may monitor and aggregate information related to clicks, time spent on articles, searches, etc. to help predict future market trends in the health and wellness and beauty industries.

Information processed by the resilience measurement system, including article clicks, reads, etc., may be used to help predict market trends in health and wellness and beauty industries and crowdsource and predict client preferences to optimize future product design and manufacturing.

Furthermore, in creating an interactive platform, depersonalized information about users can be collected to continually collect and populate aspects of certain embodiments. As data is collected, this may allow certain embodiments to become more independent of external reports and potentially update more rapidly than official reports. Additionally, the personalized or customizable nature of operations of the resilience measurement system may allow for self-reported data, which may not be reflected in official reports, adding a valuable set of information to be studied.

As certain embodiments are used, updated, and/or applied across a variety of scenarios, it can be integrated into AI/neural networks, which can collect and track data over time for predictive and/or other modeling and utilized by technologies which do not already exist.

Some of the advantages provided by the resilience measurement system can be understood through various example case studies. A first example case study may relate to a mining company that is considering initiating mining operations in a country. Processing, by the resilience measurement system of political risk measures, could be used to inform the mining company about risks of renegotiating mining rights, government transfer of rights, and cost of maintaining mining rights relative to ore prices. Furthermore, processing of, e.g., health and/or resilience measures may indicate a likelihood of disease outbreak and/or spread with respect to risks to employees that may need to be physically present in the country, a government's ability to control the outbreak, and/or what types of community engagement may be effective for strengthening relationships with the government. The resilience measurement system may process these factors to determine an overall risk profile of the country with respect to the company's decision to engage in mining operations there. Furthermore, the resilience measurement system, through analyzing risk factors, may be able to identify opportunities for investment in various communities within the country based on need and government cooperation, which can reduce risk to the company with respect to investment, reduce potential taxes, or the like.

As another example use case, the resilience measurement system may generate a country profile and may determine a political risk based on outbreaks. For example, if a country was experiencing an outbreak of one or more diseases, the resilience measurement system may process information related to the different transmission mechanisms of the disease to determine a country profile that can inform political risk considerations. The information outbreaks may indicate government or other failures even if they are not reported or are misreported. For instance, for a polio outbreak, the resilience measurement system may process information that the mechanism of transmission includes fecal or oral transmission, that the country had a small number of cases several hundred miles apart, that the disease was transmitted through water, and that the country has low vaccination rates, thus signaling a deterioration in a political institution's ability to serve its function. The resilience measurement system may also process information that polio was found in sewage, indicating poor water sanitation further highlighting risk of waterborne illness, subsequent environmental enteropathy which can cause stunting, thus indicting future economic risk and losses in GDP due to anticipated reduced productivity.

Based on this information, the resilience measurement system may identify various risks and recommendations associated with investments in the country. For instance, for a government entity, the resilience measurement system may output a recommendation to increase public health investments and address the public health gaps that can result in long-term human morbidities and mortality prevention and that the country should stop cutting its health budget, along with other weaknesses identified in subsections of the information processed. For a private sector client, the resilience measurement system may generate recommendations depending on specific client needs. For example, the resilience measurement system may generate resilience indicators and recommendations for program and/or investment adjustments, such as calculating adjustments for client change and its impact on an industry sector of the private sector client. For an NGO client, the resilience measurement system may generate reports related to observable gaps in the NGO's operations and may generate a plan or recommendation for reducing or eliminating those gaps based on grants associated with the NGO. For the country example above, the resilience measurement system may recommend to the NGO to increase expenditure and/or operations in the country for water sanitation and climate and environmental resilience programs.

In this way, the resilience measurement system may provide for resilience assessments based on industry type, which may be incorporated into a risk and opportunity score. With the example of the mining company above, health and/or location risks associated with operations and the health systems resilience of the country in the event there was an outbreak, could be processed to determine potential impacts to values associated with the organization (e.g., stock values, values of products, etc.), or for how long the value may change. The value can then, for instance, be merged with existing or in-house created ESG ranking methodologies, to create a meaningful assessment for investors and investment funds, namely, how resilient companies may be if they were impacted by a health determinant and how they should modify their operation strategies to reduce risk.

The resilience measurement system may generate recommendations related to where a company should invest, or across various locations where a company is operating. With respect to the mining company example above, the resilience measurement system may identify that the risk of a shock in one country is low due to favorable policies and other factors associated with impacts on social determinants of health, but may identify that the risk of disease outbreak in another country is much higher due to higher urbanization rates, poor water sanitation, etc. that contributed to other shock events. The resilience measurement system may use this information to generate reports or recommendations related to weaknesses in the company's preparedness based on these risks or how to mitigate health risks.

Figure 4:
FIG. 4 illustrates another example of score calculation, according to some embodiments.

FIG. 4 illustrates another example 400 of operations of the resilience measurement system, according to some embodiments. FIG. 4 illustrates a table of information that the resilience measurement system may process related to outbreak risk. The table includes scores for various risk factors for two different countries (Country A and Country B). For example, the risk factors are listed under the "Risk Factor" heading and the scores are listed under the "Country A" and "Country B" headings. In addition, the "Justification" columns may include information that identifies the reason a risk factor was assigned a score for Country A or Country B.

The scores may indicate factors which may both support stopping an outbreak and the risk of the outbreak spreading. Every score may be on a scale of, e.g., 0 to 2. A higher overall number may indicate a higher likelihood the outbreak may be severe. The basic reproduction number (Ro) value may not be factored into the total score because, in the example 400, it may make no meaningful difference since the value may be pathogen-specific and when the pathogen is the same in both countries. A pathogen may have an established reproduction number which may be a natural characteristic of the pathogen. If the pathogen is the same across multiple countries, then the Ro may be the same in those countries (unless there is a variant or some other difference in pathogens across different locations). The observed Ro can change based on risk factors like poverty, crowding, etc., resulting in a value called effective reproductive number, which may be the realized reproductive number in context. In the example 400, since the Ro may be equal among both countries, the value may be considered null for this calculation. Consideration of population density in the example 400 may replace consideration of Ro because of the role it may play in transmission dynamics.

Each factor may indicate how much the pathogen can spread, the economic impacts of the pathogen, the ability of governmental organizations in each country to get the population to cooperate with public health authorities, the ability of the government to effectively address the outbreak, and/or the like. In the example 400, because the Country B may score lower on the freedom score, it may be determined by the resilience measurement system that Country B may be able to force public health measures with less consequence. As such, in this case, the freedom score may be factored inversely to the extent that a lower score on the index may pose less of a risk than a higher rating because residents of Country B may have less freedom of choice over whether they must comply with efforts to control the pathogen. Trust in scientists may be another consideration used as a proxy to understand how much a given population values and complies with scientific authorities. In the event that a population is skeptical of scientific authorities, they may be less likely to believe that the virus is real and may not act in their best interest to reduce the spread. This may also pose an opportunity for the virus to spread, as behavior change to reduce the spread may be less likely to occur.

Population demographics may reflect the capacity of the virus to spread and the scale through which it may be able to spread based on, e.g., the age of the population, pre-existing health risks present in the population, and/or the like. Megacities may pose a particular risk because the high density of people may provide an increased opportunity for transmission. Stigma may also be considered as a factor because it may indicate the likelihood that an individual is likely to report their illness or seek medical help, to notify others that the unwell individuals may have encountered, etc.

Even in its unweighted form, the resilience measurement system may determine, from the information illustrated in FIG. 4, that Country A may have a more severe outbreak than that of Country B. The variance between the two risk values in the example 400 may be approximately 13 percent (%) though the impact of this measured risk variance is uncharacterized in this example. From an epidemiological perspective, Country B may be at a greater risk for a severe outbreak because of its population density and megacities. In the case of an outbreak, the resilience measurement system may recommend that Country B institute severe measures to prevent a severe outbreak. In certain embodiments, the resilience measurement system may learn from comparing historical data to its output to improve the accuracy of its predictions as well as time interventions and may identify where interventions could be targeted and may be most effective based on context. This may be done at the micro (e.g., community) level, and the index generated by the resilience measurement system and operations of the resilience measurement system may be scaled from the micro level to the country level (e.g., macro level), as described elsewhere herein. In this way, the resilience measurement system may help identify macro risks at, e.g., the country level as well as micro risks at, e.g., the community and individual levels and, through decision support, may identify various courses of action depending on the objective, thereby providing customized solutions.

As described above, FIG. 4 is provided as an example. Other examples are possible, according to some embodiments.

As can be understood from the example 400 and other examples described herein, effective public health response may rely on an understanding of population vulnerability, real-time data tracking to determine efficacy of interventions, and/or the like. However, rapid disaggregation of critical data reflective of the social determinants of health may be challenging to do, especially across age groups and where mechanisms of data collection are not clear. Still, data of this depth may be important for identifying groups with high transmission rates, understanding modes of transmission, and safe and effective re-opening of communities once an outbreak has been suppressed and controlled.

A rapid AI and/or ML system as described herein may be able to rapidly deploy a variety of datasets to perform scenario testing to identify and recommend time-critical interventions as well as maximize likelihood of adherence to public health measures and interventions, especially across a variety of scenarios including countries of varying income levels or other vulnerabilities. In this way, the resilience measurement system may allow for understanding public health and, more importantly, it may allow for identifying and developing effective real time responses for inevitable future outbreaks.

The resilience measurement system may aggregate data from various sources. For example, the resilience measurement system may aggregate data from social media data sets based on an AI analysis of public posts gathering data related to a ratio of outdoor and/or indoor posts over the course of the outbreak. Additionally, or alternatively, this data may be obtained through an AI analysis of public social media posts to understand mask and social distancing adherence, based on examining distance of groups and people from one another to see if people are standing apart, and/or through an AI analysis of backdrop and location identification of public posts to understand whether or not people have returned to restaurants, libraries, etc.

In certain embodiments, the resilience measurement system may aggregate fitness tracker data sets based on identifying high-risk profiles and patterns using walking step or other data related to physical activity. Additionally, or alternatively, this data may be obtained by examining changes in overall step counts, or using step data within a jurisdiction to calculate statistical risk-based on step data. For example, a person who takes 15,000 steps a day may have a risk of interacting with a high-risk contact compared to a person who takes 400 steps a day, then contrast that data with changes in steps over time. In certain embodiments, the resilience measurement system may aggregate data from fitness subscriptions, e.g., by collecting data of a new at-home fitness subscription and streaming of fitness videos (e.g., an increase in downloads and subscriptions in a given jurisdiction may indicate a level of jurisdictional adherence). In certain embodiments, the resilience measurement system may aggregate data from consumer data, e.g., by identifying clothing brands that are popular in a given jurisdiction and examining changes in online or in-person retail over time.

The resilience measurement system may overlay this data, and similar data, with demographic data such as age group, income level, likely political party affiliation, and education-level to then identify at-risk age groups, success of public health communication across age groups, and other data relevant to pandemic response. The resilience measurement system may then incorporate this information into recommendations, reports or the like, described elsewhere herein. Certain embodiments may then use publicly available data, circumventing privacy issues. In this way, the resilience measurement system may help public health officials and other decision-makers understand the efficacy of their interventions in real time, revise their approach, and learn for future responses.

Figure 5:
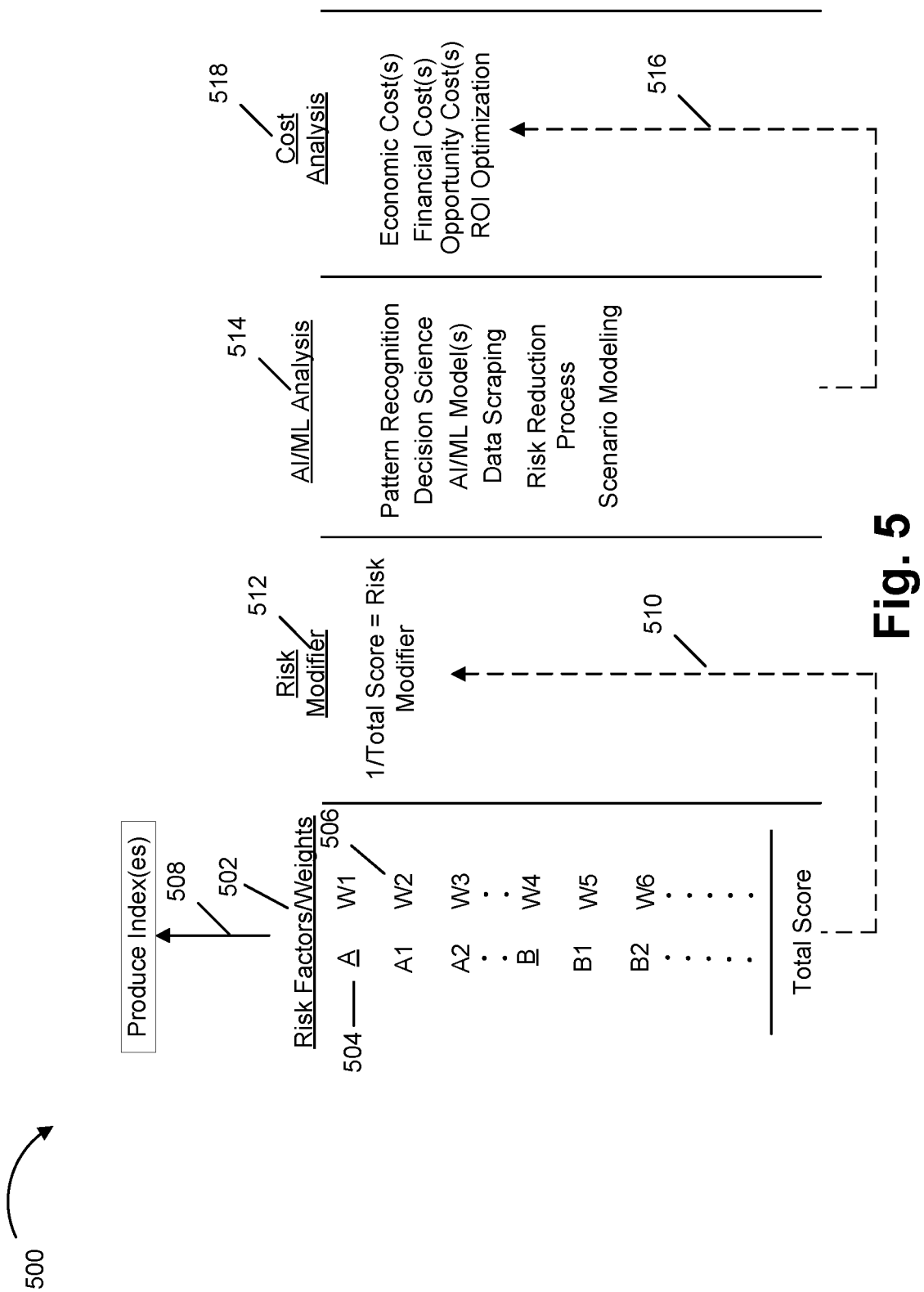
FIG. 5 illustrates another example of operations of the resilience measurement system, according to some embodiments.

FIG. 5 illustrates another example 500 of operations of the resilience measurement system, according to some embodiments. As illustrated at 502, the resilience measurement system may process information related to a set of factors measuring relevant vulnerability and resilience capacities and dynamics against one another informed by client preference, objectives, and/or weights, which may be organized into groups or categories 504 (e.g., group A, group B, etc., with the risk factors shown as A1, A2, B1, B2, etc.) to asses risk. For example, in an infectious disease outbreak scenario, capacity may be defined as the number of diagnostic labs, availability of hospital beds, health care workers, etc. available to respond to the outbreak (which may generally include people, things (e.g., ventilators, personal protective equipment, etc.), space, etc.). Continuing with the infectious disease outbreak example, dynamics may include the political, environmental, social, or other factors which might exacerbate or mitigate the outbreak. For example, if a government were unwilling to exercise use of the labs or fund a response, this may exacerbate the size of the outbreak (e.g., in terms of the number of individuals who contract the disease or die from the disease, the number of geographic areas impacted by the disease, etc.). If social factors like stigma made people unwilling to report illness or wear a mask, these could exacerbate the outbreak as well. These factors can mitigate the outbreak when they work in reverse. For example, sufficient social cohesion may make the population more cooperative and careful to wear masks; a strong government may make mobilizing a response more likely; etc. Certain embodiments described herein may apply to various other scenarios and other determinants of health, resilience, one health, etc. For example, in a heart disease scenario, the resilience measurement system may process information related to urbanization rate, inequality, size of populations living in food deserts, etc. in a manner similar to that described above for the infectious disease scenario. In this way, certain embodiments described herein provide advantages over other models by measuring capacity against dynamics (e.g., financial considerations, air quality considerations, trust in science, etc.) while other models may emphasize capacity without penalizing for, e.g., poor dynamic setup, such as uninterested governments.

Each of the factors may be associated with a weight 506 (e.g., weights W2 for A1, etc.), and the groups or categories 504 may also have corresponding weights (e.g., W1 for group A, etc.). The weights may be subject to user or client discretion and/or user or client objectives. The operations of the resilience measurement system related to the factors and/or weights may use data scraping to, e.g., determine the weights from third party sources. As illustrated at 508, the resilience measurement system may produce one or more indexes based on the factors and/or weights associated with the risk factors (e.g., a short term index (less than 2 years), medium term index (2-7 years), or long term index (7+ years) using projections). As illustrated at 510, the resilience measurement system may determine a total score for the factors based on the weights and values for the factors (the total score may be a resilience score), and may use this total score to determine the risk modifier at 512. For example, a value may be divided by the total score, may be multiplied by the total score, etc. to determine the risk modifier. The risk modifier can be used by the resilience measurement system to determine a value of a stock, to determine a risk for insurance purposes, for risk assessments of an investment, and/or the like. The risk modifier may not be needed for scenario modeling but may be used for recommendations and/or cost analyses described elsewhere herein.

As illustrated at 514, the resilience measurement system may perform an AI and/or ML analysis that uses, e.g., pattern recognition, decision science, AI and/or ML models, data scraping, a risk reduction process, and/or scenario modeling, as described elsewhere herein. For example, risk reduction can be used for operational risk reduction, insurance purposes, policy and/or country recommendations, opportunity mapping, and/or opportunity maximization. As illustrated at 516, the resilience measurement system may use an output from the AI and/or ML analysis to perform a cost analysis at 518. Similar to that described elsewhere herein, the cost analysis at 518 may include an analysis of economic cost(s), financial cost(s), opportunity cost(s), value for money (e.g., using money at a particular time for a particular service), and/or ROI optimization. The cost analysis may be performed for the short term (e.g., less than 2 years), the medium term (e.g., 2-7 years), and/or the long term (e.g., 7+ years). The analyses at 514 and/or 518 may use data scraping for, e.g., scenario modeling.

As indicated above, FIG. 5 is provided merely as an example. Other examples are possible according to certain embodiments. Although FIGS. 2 and 5 illustrate examples of how certain embodiments can be utilized for resilience or public health-related risk factors at a macro scale, certain embodiments may be applied to a single risk factor (or category of risk factors), such as climate and environmental risk. It is also possible for certain embodiments to process information at the individual level (e.g., where individual health data is processed), at the community level, the country level, the regional level, and the global level.

Figure 6:
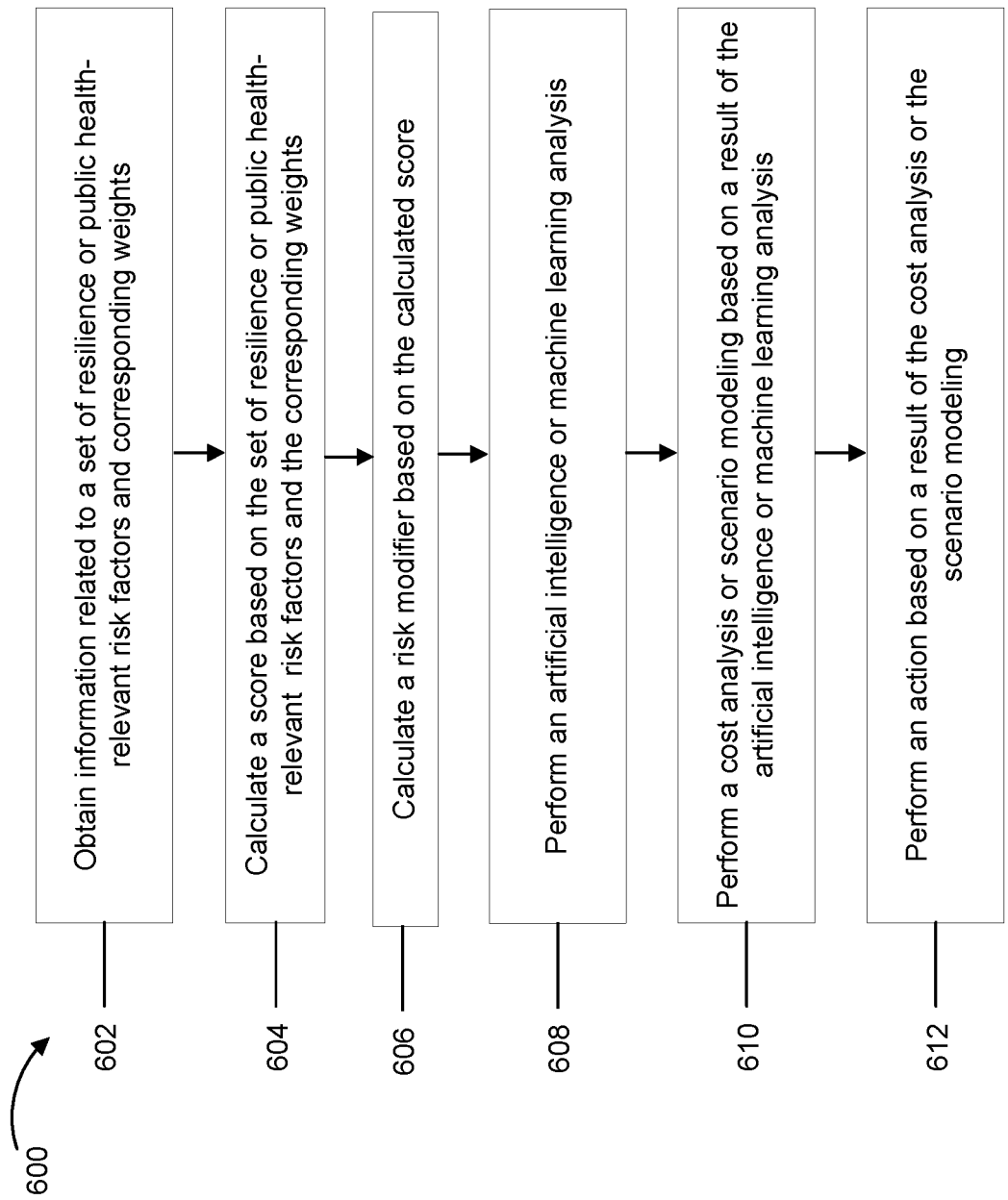
FIG. 6 illustrates an example flow diagram of a method, according to some embodiments.

FIG. 6 illustrates an example flow diagram of a method 600, according to some embodiments. For example, FIG. 6 may illustrate example operations of a resilience measurement system (e.g., apparatus 10 illustrated in, and described with respect to, FIG. 7). Some of the operations illustrated in FIG. 6 may be similar to some operations shown in, and described with respect to, FIGS. 1-4.

In an embodiment, the method may include, at 602, obtaining information related to a set of resilience or public health-relevant risk factors and corresponding weights, e.g., in a manner similar to that at 102 of FIG. 1. The method may include, at 604, calculating a score based on the set of resilience or public health-relevant risk factors and the corresponding weights, e.g., in a manner similar to that at 104 of FIG. 1. The method may include, at 606, calculating a risk modifier based on the calculated score, e.g., in a manner similar to that at 106 of FIG. 1. The method may include, at 608, performing an artificial intelligence or machine learning analysis, e.g., in a manner similar to that 108 of FIG. 1. The method may include, at 610, performing a cost analysis or scenario modeling based on a result of the artificial intelligence or machine learning analysis, e.g., in a manner similar to that at 110 of FIG. 1. In certain embodiments, the method may include performing a risk reduction, an opportunity maximization, or a cost reduction based on the cost or value for money analysis or the scenario modeling. The performing of the artificial intelligence or machine learning analysis at 608 or the performing of the cost analysis at 610 may include performing pattern recognition, performing the scenario modeling, performing predictive modeling, or performing another type of analysis. The method may include, at 612, performing an action based on a result of the cost analysis or the scenario modeling, e.g., in a manner similar to that 112 or 114 of FIG. 1.

The method illustrated in FIG. 6 may include one or more additional aspects described below or elsewhere herein. In some embodiments, the obtaining at 602 may include obtaining the information by querying the information, by receiving a push of the information, by scraping a website, or via a user interface associated with the resilience measurement system. In some embodiments, the calculating at 604 may include calculating the score by multiplying the corresponding weights by scores for the set of resilience or public health-relevant risk factors and processing the scores for the set of resilience or public health-relevant risk factors (e.g., the method may include averaging the scores, subtracting one or more scores from one or more other scores (e.g., when assessing capacity to response versus transmission dynamics, or other factors that counter each other), etc.). In certain embodiments, the method may include performing statistical modeling or scenario modeling to assess a likelihood of an event occurring within a given time period (e.g., after obtaining the information, the resilience measurement system may perform a Monte Carlo simulation where a scenario is tested multiple times to determine which event(s) are more likely to occur than other events). In some embodiments, the set of resilience or public health-relevant risk factors may include one or more of the following, outbreak risk factors, climate and environmental risk factors, human health risk factors, country profile risk factors, political risk factors, institutional integrity risk factors, operational risk factors, one health risk factors, or financial risk factors.

In some embodiments, the method may further include determining an index for estimated lost gross domestic product or economic costs based on the resilience or public health-relevant risk factors. In some embodiments, the performing at 612 may include outputting, to an output device, the result of the cost analysis or the scenario modeling for storage or display. In some embodiments, the performing at 612 may include communicating with a server device to rebalance an investment portfolio or rate stocks or other assets (e.g., currencies, equities, etc.) based on the result of the result of the cost analysis or the scenario modeling.

In some embodiments, the calculating at 606 may include processing (e.g., dividing, multiplying, etc.) a value by the score, wherein the score is a total score based on scores for the set of resilience or public resilience or public health-relevant risk factors. In some embodiments, the performing at 610 may include performing the artificial intelligence or machine learning analysis using at least one of: the pattern recognition, decision science, an artificial intelligence or machine learning model, data scraping, a risk reduction process, an opportunity maximization, the scenario modeling, or one or more types of simulations (e.g., Monte Carlo simulation, or the like) to calculate statistical likelihoods. In some embodiments, the method may further include determining a rating for a security or an asset based on the risk modifier.

In some embodiments, the performing at 610 may include performing the cost analysis of at least one of: one or more economic costs, one or more financial costs, one or more opportunity costs, value for money, a return on investment optimization, or opportunity identification. In some embodiments, the performing at 610 may include performing the scenario modeling to identify a plan of action (e.g., when the objective of the resilience measurement system is to avoid risk or identify possible interventions for an organization, the resilience measurement system may perform scenario modeling to identify one or more plans of action to avoid the risk, may prioritize various plans of action, etc.) In some embodiments, the performing the action at 612 may include generating a recommendation related to an investment or a strategic resource allocation, and outputting the recommendation for display via an output device. In some embodiments, the calculating at 606 may include calculating scores for sub-risk factors of each of the set of resilience or public health-relevant risk factors, calculating scores for each of the set of resilience or public health-relevant risk factors based on the scores for the sub-risk factors, and calculating the score for the set of resilience or public health-relevant risk factors based on the scores for each of the set of resilience or public health-relevant risk factors.

In some embodiments, the performing at 610 may include performing the cost analysis of at least one of: one or more economic costs, one or more financial costs, one or more opportunity costs, a return on investment optimization, an opportunity maximization, or a risk minimization. In some embodiments, the performing at 608 may include performing a Monte Carlo simulation, or the like (e.g., to assess a likelihood of an event occurring within a given timeframe).

As described above, FIG. 6 is provided as an example. Other examples are possible according to some embodiments.

Certain embodiments described herein may be applied to a single subset of resilience or public health-relevant risk factors, such as climate and environmental risk, outbreak risk, a country profile, and/or the like, and may utilize any of the actions described herein. Certain embodiments described herein may utilize and/or process structured or unstructured data. The data may include thousands, millions, billions, or trillions of data elements. In certain embodiments, the resilience measurement system may perform pattern recognition or the like on the data, and may correlate changes in the data with indications of an occurrence of an event, and may communicate a recommendation or other decision support information. This information may include economic costs, financial costs, opportunity costs, a return on investment optimization, an opportunity maximization, or a risk minimization.

Certain embodiments described herein can be performed at an various levels, such as an individual, community, jurisdictional, country, regional, or global level based on inputs to the resilience measurement system. For example, when certain operations described herein are performed for the individual, the decision support that the resilience measurement system might provide may include recommendations to reduce individual health risks, such as, e.g., cessation of smoking, increasing consumption of high fiber foods, etc.

Figure 7:
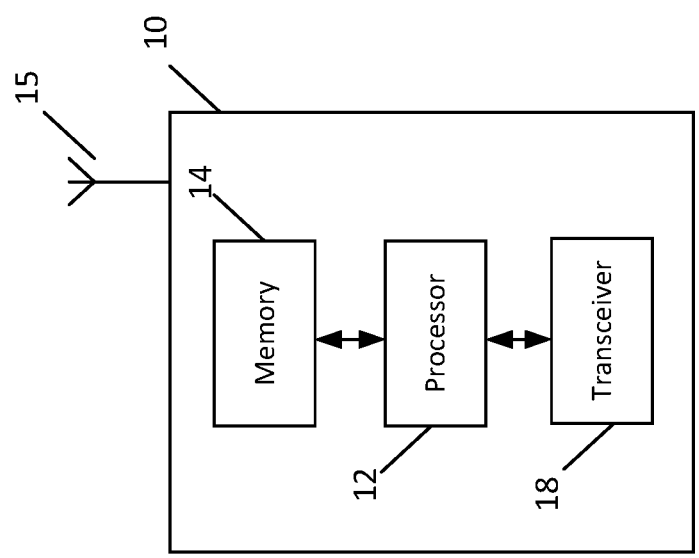
FIG. 7 illustrates an example block diagram of an apparatus, according to an embodiment.

FIG. 7 illustrates an example of an apparatus 10 according to an embodiment. In an embodiment, apparatus 10 may be a node, host, or server in a communications network or serving such a network. For example, apparatus 10 may be computing device (e.g., a computing device associated with a resilience measurement system or an output device), and/or the like. One or more apparatuses 10 may be connected via a wired network, a wireless network, or a combination of wired and wireless networks.

As illustrated in the example of FIG. 7, apparatus 10 may include a processor 12 for processing information and executing instructions or operations. Processor 12 may be any type of general or specific purpose processor. In fact, processor 12 may include one or more of general-purpose computers, special purpose computers, microprocessors, digital signal processors (DSPs), field-programmable gate arrays (FPGAs), application-specific integrated circuits (ASICs), and processors based on a multi-core processor architecture, as examples. While a single processor 12 is shown in FIG. 7, multiple processors may be utilized according to other embodiments. For example, it should be understood that, in certain embodiments, apparatus 10 may include two or more processors that may form a multiprocessor system (e.g., in this case processor 12 may represent a multiprocessor) that may support multiprocessing. In certain embodiments, the multiprocessor system may be tightly coupled or loosely coupled (e.g., to form a computer cluster).

Processor 12 may perform functions associated with the operation of apparatus 10, which may include, for example, precoding of antenna gain/phase parameters, encoding and decoding of individual bits forming a communication message, formatting of information, and overall control of the apparatus 10, including processes related to management of communication or communication resources.

Apparatus 10 may further include or be coupled to a memory 14 (internal or external), which may be coupled to processor 12, for storing information and instructions that may be executed by processor 12. Memory 14 may be one or more memories and of any type suitable to the local application environment, and may be implemented using any suitable volatile or nonvolatile data storage technology such as a semiconductor-based memory device, a magnetic memory device and system, an optical memory device and system, fixed memory, and/or removable memory. For example, memory 14 can be comprised of any combination of random access memory (RAM), read only memory (ROM), static storage such as a magnetic or optical disk, hard disk drive (HDD), or any other type of non-transitory machine or computer readable media. The instructions stored in memory 14 may include program instructions or computer program code that, when executed by processor 12, enable the apparatus 10 to perform tasks as described herein.

In an embodiment, apparatus 10 may further include or be coupled to (internal or external) a drive or port that is configured to accept and read an external computer readable storage medium, such as an optical disc, USB drive, flash drive, or any other storage medium. For example, the external computer readable storage medium may store a computer program or software for execution by processor 12 and/or apparatus 10.

In some embodiments, apparatus 10 may also include or be coupled to one or more antennas 15 for transmitting and receiving signals and/or data to and from apparatus 10. Apparatus 10 may further include or be coupled to a transceiver 18 configured to transmit and receive information. The transceiver 18 may include, for example, a plurality of radio interfaces that may be coupled to the antenna(s) 15. The radio interfaces may correspond to a plurality of radio access technologies including one or more of GSM, NB-IoT, LTE, 5G, WLAN, Bluetooth, BT-LE, NFC, radio frequency identifier (RFID), ultrawideband (UWB), Multe-Fire, and the like. The radio interface may include components, such as filters, converters (for example, digital-to-analog converters and the like), mappers, a Fast Fourier Transform (FFT) module, and the like, to generate symbols for a transmission via one or more downlinks and to receive symbols (for example, via an uplink).

As such, transceiver 18 may be configured to modulate information on to a carrier waveform for transmission by the antenna(s) 15 and demodulate information received via the antenna(s) 15 for further processing by other elements of apparatus 10. In other embodiments, transceiver 18 may be capable of transmitting and receiving signals or data directly. Additionally or alternatively, in some embodiments, apparatus 10 may include an input and/or output device (I/O device).

In an embodiment, memory 14 may store software modules that provide functionality when executed by processor 12. The modules may include, for example, an operating system that provides operating system functionality for apparatus 10. The memory may also store one or more functional modules, such as an application or program, to provide additional functionality for apparatus 10. The components of apparatus 10 may be implemented in hardware, or as any suitable combination of hardware and software.

According to some embodiments, processor 12 and memory 14 may be included in or may form a part of processing circuitry or control circuitry. In addition, in some embodiments, transceiver 18 may be included in or may form a part of transceiver circuitry.

As used herein, the term "circuitry" may refer to hardware-only circuitry implementations (e.g., analog and/or digital circuitry), combinations of hardware circuits and software, combinations of analog and/or digital hardware circuits with software/firmware, any portions of hardware processor(s) with software (including digital signal processors) that work together to cause an apparatus (e.g., apparatus 10) to perform various functions, and/or hardware circuit(s) and/or processor(s), or portions thereof, that use software for operation but where the software may not be present when it is not needed for operation. As a further example, as used herein, the term "circuitry" may also cover an implementation of merely a hardware circuit or processor (or multiple processors), or portion of a hardware circuit or processor, and its accompanying software and/or firmware. The term circuitry may also cover, for example, a baseband integrated circuit in a server, cellular network node or device, or other computing or network device.

As introduced above, in certain embodiments, apparatus 10 may be a computing device, a resilience measurement system, or an output device.

According to certain embodiments, apparatus 10 may be controlled by memory 14 and processor 12 to perform the functions associated with any of the embodiments described herein, such as some operations illustrated in, or described with respect to, FIGS. 1-5. For instance, apparatus 10 may be controlled by memory 14 and processor 12 to perform the method of FIG. 6.

In some embodiments, an apparatus (e.g., apparatus 10) may include means for performing a method or any of the variants discussed herein, e.g., a method described with reference to FIG. 6. Examples of the means may include one or more processors, memory, and/or computer program code for causing the performance of the operation.

Therefore, certain example embodiments provide several technological improvements, enhancements, and/or advantages over existing technological processes. For example, one benefit of some example embodiments is more complex, faster, and more accurate analysis than otherwise possible, or more efficient analysis (which conservers computing resources). Accordingly, the use of some example embodiments results in improved functioning of communications networks and their nodes and, therefore constitute an improvement at least to the technological field of analysis support systems, among others.

In some example embodiments, the functionality of any of the methods, processes, signaling diagrams, algorithms or flow charts described herein may be implemented by software and/or computer program code or portions of code stored in memory or other computer readable or tangible media, and executed by a processor.

In some example embodiments, an apparatus may be included or be associated with at least one software application, module, unit or entity configured as arithmetic operation(s), or as a program or portions of it (including an added or updated software routine), executed by at least one operation processor. Programs, also called program products or computer programs, including software routines, applets and macros, may be stored in any apparatus-readable data storage medium and may include program instructions to perform particular tasks.

A computer program product may include one or more computer-executable components which, when the program is run, are configured to carry out some example embodiments. The one or more computer-executable components may be at least one software code or portions of code. Modifications and configurations used for implementing functionality of an example embodiment may be performed as routine(s), which may be implemented as added or updated software routine(s). In one example, software routine(s) may be downloaded into the apparatus.

As an example, software or a computer program code or portions of code may be in a source code form, object code form, or in some intermediate form, and it may be stored in some sort of carrier, distribution medium, or computer readable medium, which may be any entity or device capable of carrying the program. Such carriers may include a record medium, computer memory, read-only memory, photoelectrical and/or electrical carrier signal, telecommunications signal, and/or software distribution package, for example. Depending on the processing power needed, the computer program may be executed in a single electronic digital computer or it may be distributed amongst a number of computers. The computer readable medium or computer readable storage medium may be a non-transitory medium.

In other example embodiments, the functionality may be performed by hardware or circuitry included in an apparatus (e.g., apparatus 10), for example through the use of an application specific integrated circuit (ASIC), a programmable gate array (PGA), a field programmable gate array (FPGA), or any other combination of hardware and software. In yet another example embodiment, the functionality may be implemented as a signal, such as a non-tangible means that can be carried by an electromagnetic signal downloaded from the Internet or other network.

According to an example embodiment, an apparatus, such as a node, device, or a corresponding component, may be configured as circuitry, a computer or a microprocessor, such as single-chip computer element, or as a chipset, which may include at least a memory for providing storage capacity used for arithmetic operation(s) and/or an operation processor for executing the arithmetic operation(s).

Example embodiments described herein apply equally to both singular and plural implementations, regardless of whether singular or plural language is used in connection with describing certain embodiments. For example, an embodiment that describes operations of a single resilience measurement system (or a computing device thereof) equally applies to embodiments that include multiple instances of the resilience measurement system (or a computing device thereof), and vice versa. In addition, certain embodiments described herein may be applicable to a wide variety of contexts, such as insurance (e.g., for business operations), business operations (e.g., optimizing those operations and risk mitigation), financial sectors (e.g., identifying risk and reducing investment), government sectors (e.g., identifying health risks and opportunities for investment, domestically and abroad), trade-offs (e.g., identifying trade-offs to help optimize ROI), and/or opportunity maximization (e.g., using decision science to identify opportunities and ways to maximize them). Additionally, or alternatively, certain embodiments may be used in a variety of ways in addition to, or different than, those described elsewhere herein. For example, because the resilience measurement system may gather a large amount of data, the resilience measurement system may use an AI and/or ML model, in connection with, e.g., pattern recognition or the like, to predict trends in various industries, such as health, wellness, beauty, etc., may identify which products might do well in an area, and may recommend products to individuals based on predicted events, characteristics of the individuals, etc. in that area.

One having ordinary skill in the art will readily understand that the example embodiments as discussed above may be practiced with operations in a different order, and/or with hardware elements in configurations which are different than those which are disclosed. Therefore, although some embodiments have been described based upon these example embodiments, it would be apparent to those of skill in the art that certain modifications, variations, and alternative constructions would be apparent, while remaining within the spirit and scope of example embodiments.

I claim:

1. A method, comprising:
   obtaining, by a resilience measurement system, information related to a set of public health-relevant risk factors in the form of structured and unstructured data from one or more computing devices different than the resilience measurement system and corresponding weights via a user interface associated with the resilience measurement system;
   calculating a score based on the set of public health-relevant risk factors and the corresponding weights;
   calculating a risk modifier based on the calculated score;
   performing statistical modeling or scenario modeling using a generative adversarial network according to the risk modifier calculated based on the calculated score to assess a likelihood of an event occurring within a given time period;
   performing an artificial intelligence or machine learning analysis using one or more models trained to process baseline data for a scenario and the risk modifier;
   performing a cost analysis or scenario modeling based on a result of the artificial intelligence or machine learning analysis and performing a risk reduction, an opportunity maximization, or a cost reduction based on the cost analysis or the scenario modeling;
   performing, by the resilience measurement system, an action based on a result of the cost analysis or the scenario modeling; and
   based upon at least one user preference, generating a recommended user action associated with the at least one received objective.

2. The method according to claim 1, wherein the obtaining of the information further comprises:
   obtaining the information by querying the information from the one or more computing devices, by receiving a push of the information from the one or more computing devices, by scraping a website hosted on the one or more computing devices, or via the user interface associated with the resilience measurement system.

3. The method according to claim 1, wherein the calculating of the score further comprises:
   calculating the score by multiplying the corresponding weights by scores for the set of public health-relevant risk factors and processing the scores for the set of public health-relevant risk factors.

4. The method according to claim 1, wherein the set of public health-relevant risk factors include at least one of:
   outbreak risk factors,
   climate and environmental risk factors,
   human health risk factors,
   country profile risk factors,
   political risk factors,
   institutional integrity risk factors,
   one health risk factors,
   operational risk factors, or
   financial risk factors.

5. The method according to claim 1, further comprising:
determining an index for estimated lost gross domestic product or economic costs based on the public health-relevant risk factors.

6. The method according to claim 1, wherein the performing of the action further comprises:
outputting, to an output device, the result of the cost analysis or the scenario modeling for storage or display.

7. The method according to claim 1, wherein the performing of the action further comprises:
communicating with a server device to rebalance an investment portfolio or rate stocks or other assets based on the result of the result of the cost analysis or the scenario modeling.

8. The method according to claim 1, wherein the statistical modeling or scenario modeling is performed using generative adversarial network generated scenarios.

9. An apparatus, comprising:
at least one processor; and
at least one memory including computer program code, wherein the at least one memory and the computer program code are configured to, with the at least one processor, cause the apparatus at least to:
obtain information related to a set of public health-relevant risk factors in the form of structured and unstructured data from one or more computing devices different than the resilience measurement system and corresponding weights via a user interface associated with the resilience measurement system;
calculate a score based on the set of public health-relevant risk factors and the corresponding weights;
calculate a risk modifier based on the calculated score;
perform statistical modeling or scenario modeling using a generative adversarial network according to the risk modifier calculated based on the calculated score to assess a likelihood of an event occurring within a given time period;
perform an artificial intelligence or machine learning analysis using one or more models trained to process baseline data for a scenario and the risk modifier;
perform a cost analysis or scenario modeling based on a result of the artificial intelligence or machine learning analysis and performing a risk reduction, an opportunity maximization, or a cost reduction based on the cost analysis or the scenario modeling;
perform, by the apparatus, an action based on a result of the cost analysis or the scenario modeling; and
based upon at least one user preference, generate a recommended user action associated with the at least one received objective.

10. The apparatus according to claim 9, wherein the at least one memory and the computer program code are configured to, with the at least one processor, further cause the apparatus, when calculating the risk modifier, at least to:
process a value by the score, wherein the score is a total score based on scores for the set of public health-relevant risk factors.

11. The apparatus according to claim 9, wherein the at least one memory and the computer program code are configured to, with the at least one processor, further cause the apparatus, when performing the artificial intelligence or machine learning analysis, at least to:
perform the artificial intelligence or machine learning analysis using at least one of:
pattern recognition,
decision science,
an artificial intelligence or machine learning model,
data scraping,
a risk reduction process,
an opportunity maximization, or
the scenario modeling.

12. The method according to claim 9, wherein the at least one memory and the computer program code are configured to, with the at least one processor, further cause the apparatus at least to:
determine a rating for a security, currency, or an asset based on the risk modifier.

13. The apparatus according to claim 9, wherein the at least one memory and the computer program code are configured to, with the at least one processor, further cause the apparatus, when performing the cost analysis, at least to:
perform the cost analysis of at least one of:
one or more economic costs,
one or more financial costs,
one or more opportunity costs,
value for money,
a return on investment optimization, or
opportunity identification.

14. The apparatus according to claim 9, wherein the at least one memory and the computer program code are configured to, with the at least one processor, further cause the apparatus, when performing the action, at least to:
generate a recommendation related to an investment, modification to business operations, or strategic resource allocation for maximum benefit, efficacy, or return on investment; and
output the recommendation for display via an output device.

15. The method according to claim 9, wherein the at least one memory and the computer program code are configured to, with the at least one processor, further cause the apparatus, when calculating the score, at least to:
calculate scores for sub-risk factors of each of the set of public health-relevant risk factors;
calculate scores for each of the set of public health-relevant risk factors based on the scores for the sub-risk factors; and
calculate the score for the set of public health-relevant risk factors based on the scores for each of the set of public health-relevant risk factors.

16. A non-transitory computer readable medium comprising program instructions for causing an apparatus to perform at least the following:
obtaining information related to a set of public health-relevant risk factors in the form of structured and unstructured data from one or more computing devices different than the resilience measurement system and corresponding weights via a user interface associated with the resilience measurement system;
calculating a score based on the set of public health-relevant risk factors and the corresponding weights;
calculating a risk modifier based on the calculated score;
performing statistical modeling or scenario modeling using a generative adversarial network according to the risk modifier calculated based on the calculated score to assess a likelihood of an event occurring within a given time period;
performing an artificial intelligence or machine learning analysis using one or more models trained to process baseline data for a scenario and the risk modifier;
performing a cost analysis or scenario modeling based on a result of the artificial intelligence or machine learning analysis and performing a risk reduction, an opportunity maximization, or a cost reduction based on the cost analysis or the scenario modeling;

performing, by the apparatus, an action based on a result of the cost analysis;

recommending, by the apparatus, a risk reduction strategy or identification of an opportunity; and based upon at least one user preference, generating a recommended user action associated with the at least one received objective.

17. The non-transitory computer readable medium according to claim 16, wherein the program instructions further comprise program instructions for causing the apparatus, when obtaining the information, to perform at least the following:

obtaining the information by querying the information from the one or more computing devices, by receiving a push of the information from the one or more computing devices, by scraping a website hosted on the one or more computing devices, or via the user interface associated with the resilience measurement system.

18. The non-transitory computer readable medium according to claim 16, wherein the program instructions further comprise program instructions for causing the apparatus, when calculating the score, to perform at least the following:

calculating the score by multiplying the corresponding weights by scores for the set of public health-relevant risk factors and processing the scores for the set of public health-relevant risk factors.

19. The non-transitory computer readable medium according to claim 16, wherein the program instructions further comprise program instructions for causing the apparatus, when calculating the risk modifier, to perform at least the following:

processing a value by the score, wherein the score is a total score based on scores for the set of public health-relevant risk factors.

20. The non-transitory computer readable medium according to claim 16, wherein the program instructions further comprise program instructions for causing the apparatus, when performing the artificial intelligence or machine learning analysis, to perform at least the following:

performing the artificial intelligence or machine learning analysis using at least one of:
pattern recognition,
decision science,
an artificial intelligence or machine learning model,
data scraping,
a risk reduction process,
a cost reduction process,
an opportunity maximization,
value for money,
the scenario modeling, or
one or more types of simulations to calculate statistical likelihoods.

21. The non-transitory computer readable medium according to claim 16, wherein the program instructions further comprise program instructions for causing the apparatus, when performing the cost analysis, to perform at least the following:

performing the cost analysis of at least one of:
one or more economic costs,
one or more financial costs,
one or more opportunity costs,
a return on investment optimization,
value for money,
an opportunity maximization, or
a risk minimization.

22. The non-transitory computer readable medium according to claim 16, wherein the program instructions further comprise program instructions for causing the apparatus, when performing the artificial intelligence or machine learning analysis, to perform at least the following:

performing a Monte Carlo simulation.

* * * * *